US010695295B2

(12) United States Patent
Lichty et al.

(10) Patent No.: US 10,695,295 B2
(45) Date of Patent: Jun. 30, 2020

(54) SPRAY-DRIED PHARMACEUTICAL COMPOSITIONS COMPRISING ACTIVE AGENT NANOPARTICLES

(71) Applicant: Besins Healthcare Luxembourg SARL, Luxembourg (LU)

(72) Inventors: Maynard Emanuel Lichty, Durham, NC (US); Garry T. Gwozdz, Jim Thorpe, PA (US)

(73) Assignee: BESINS HEALTHCARE LUXEMBOURG SARL, Luxembourg (LU)

( * ) Notice: Subject to any disclaimer, the term of this patent is extended or adjusted under 35 U.S.C. 154(b) by 0 days.

(21) Appl. No.: 14/195,023

(22) Filed: Mar. 3, 2014

(65) Prior Publication Data

US 2014/0248367 A1 Sep. 4, 2014

Related U.S. Application Data

(60) Provisional application No. 61/772,095, filed on Mar. 4, 2013.

(51) Int. Cl.
*A61K 9/16* (2006.01)
*A61K 9/14* (2006.01)
*A61K 31/57* (2006.01)
*A61K 9/00* (2006.01)

(52) U.S. Cl.
CPC .......... *A61K 9/1652* (2013.01); *A61K 9/0034* (2013.01); *A61K 9/0043* (2013.01); *A61K 9/14* (2013.01); *A61K 9/1682* (2013.01); *A61K 31/57* (2013.01)

(58) Field of Classification Search
None
See application file for complete search history.

(56) References Cited

U.S. PATENT DOCUMENTS

| 6,221,379 | B1 * | 4/2001 | Place | A61K 9/006 |
| | | | | 424/435 |
| 6,906,027 | B2 | 6/2005 | Oki et al. | |
| 7,638,138 | B2 | 12/2009 | Oki et al. | |
| 2002/0012688 | A1 * | 1/2002 | Dohi | A61K 9/0043 |
| | | | | 424/434 |
| 2007/0031490 | A1 | 2/2007 | Loebenberg et al. | |
| 2010/0178331 | A1 | 7/2010 | Nagata et al. | |
| 2011/0250274 | A1 * | 10/2011 | Shaked | A61K 9/006 |
| | | | | 424/484 |

FOREIGN PATENT DOCUMENTS

| EP | 0 122 036 A1 | 10/1984 |
| EP | 1 108 423 A1 | 6/2001 |
| EP | 1 598 066 A1 | 11/2005 |
| EP | 1 785 145 A1 | 5/2007 |
| EP | 2 116 264 A1 | 11/2009 |
| JP | 2003-523954 A | 8/2003 |
| JP | 2006-516616 A | 7/2006 |
| WO | WO-01/41760 A2 | 6/2001 |
| WO | WO-2004/067004 A1 | 8/2004 |
| WO | WO 2007/070851 A2 | 6/2007 |
| WO | WO-2007/117661 | 10/2007 |
| WO | WO 2008/075102 A1 | 6/2008 |
| WO | WO 2010/131486 A1 | 11/2010 |
| WO | WO-2012/051426 A2 | 4/2012 |
| WO | WO 2013/006333 A1 | 1/2013 |

OTHER PUBLICATIONS

Chaturvedi et al. (A review on mucoadhesive polymer used in nasal delivery system, J Adv Pharm Technol Res (Oct.-Dec. 2011), v.2 (4): 215-222), 9 pages.*
FMC (FMC Health and Nutrition, Avicel® for Solid Dosage Forms, [Downloaded from internet <URL: http://www.fmcbiopolymer.com/Pharmaceutical/Products/Avicelforsoliddoseforms.aspx>]; [Retrieved Jan. 29, 2016], 2 pages).*
FMC BioPolymer, MSDS, Avicel® PH Microcrystalline Cellulose (Jan. 31, 2008), [Retrieved from internet <URL: http://www.fmcbiopolymer.com/Portals/Pharm/Content/Docs/avicelphmsds.pdf>], 9 pages.*
FMC BioPolymer, MSDS for Ac-Di-Sol® SD-711 Croscarmellose Sodium (Feb. 5, 2008), [Retrieved from internet <URL: http://www.fmcbiopolymer.com/Portals/Pharm/Content/Docs/acdisolmsds.pdf>], 9 pages.*
Fransén et al. (Development and characterization of interactive mixtures with a fine-particulate mucoadhesive carrier for nasal delivery, European Journal of Pharmaceutics and Biopharmaceutics (2007) 67: 370-376).*
Jain et al. (Solubility Enhancements by Solvent Deposition Technique: An Overview, Asian Journal of Pharmaceutical and Clinical Research (2012) (Note, document revised and accepted for publication Oct 22, 2012), vol. 5, Suppl. 4, pp. 15-19).*
Shihora et al. (Superdisintegrants, Utility in Dosage Forms: A Quick Review, Journal of Pharmaceutical Science and Bioscientific Research (JPSBR), (Nov.-Dec. 2011), vol. 1, Issue 3, pp. 148-153).*
PubChem, Estriol, [Retrieved from internet <URL: https://pubchem.ncbi.nlm.nih.gov/compound/estriol>], [Downloaded Dec. 30, 2017], 11 pages (Year: 2017).*

(Continued)

*Primary Examiner* — Jennifer A Berrios
(74) *Attorney, Agent, or Firm* — Foley & Lardner LLP

(57) ABSTRACT

Provided herein are dry pharmaceutical compositions for transmucosal delivery, comprising spray-dried particles that include pharmaceutically active agent nanoparticles, a binder, and a pharmaceutically acceptable carrier, where the active agent nanoparticles have an average particle size diameter prior to spray-drying of less than about 1 μm, and wherein up to 10% of the spray-dried particles have a particle size of less than 10 μm; at least 50% of the spray-dried particles have a particle size of at least about 15 μm; and at least 90% of the spray-dried particles have a particle size of up to about 55 μm. Also provided are methods for making such pharmaceutical compositions and therapeutic methods comprising transmucosally administering the compositions, such as intranasally or intravaginally.

21 Claims, 8 Drawing Sheets

(56) References Cited

OTHER PUBLICATIONS

PubChem, Progesterone, [Retrieved from internet <URL: https://pubchem.ncbi.nlm.nih.gov/compound/progesterone >], [Downloaded Dec. 30, 2017], 11 pages (Year: 2017).*
WIPO, Certified copy of priority document for Shaked et al, U.S. Appl. No. 13/063,803 and PCT/US2009/057524, U.S. Appl. No. 61/098,615, priority document for U.S. Appl. No. 13/063,803 by Shaked et al. (65 pages) (Year: 2008).*
International Search Report dated May 30, 2014 in application No. PCT/US2014/019833.
Chaturvedi et al., "A review on mucoadhesive polymer used in nasal drug system," Journal of Advanced Pharmaceutical Technology & Research, vol. 2, No. 4, pp. 215-222, Oct.-Dec. 2011.

* cited by examiner

… …

SPRAY-DRIED PHARMACEUTICAL COMPOSITIONS COMPRISING ACTIVE AGENT NANOPARTICLES

RELATED APPLICATION

This application claims priority under 35 U.S.C. § 119(e) to U.S. Provisional Application No. 61/772,095, filed Mar. 4, 2013, the entire contents of which is incorporated herein by reference.

FIELD

Described herein are dry pharmaceutical compositions for transmucosal administration, such as intranasal administration or intravaginal administration, comprising spray-dried particles that comprise active agent nanoparticles, binder, and a pharmaceutically acceptable carrier. Also described are methods for making and using such compositions.

BACKGROUND

Many active agents used for systemic effect are administered intravenously. However, intravenous administration can be inconvenient and requires special medical equipment and trained health care providers. Moreover, many intravenous formulations are unstable and must be prepared shortly before use. Transmucosal administration, such as intranasal administration or intravaginal administration, offer alternatives to intravenous administration. However, transmucosal administration requires careful formulation. For example, compositions for intranasal administration should promote absorption of active agent via the nasal mucosae rather than through a pulmonary route.

Many different therapeutic uses of progesterone are known. For example, progesterone can be used to regulate the menstrual cycle, to support the luteal phase in in vitro fertilization methods, and in hormone replacement therapy. Compositions for intravaginal administration may be particular suited for these and similar uses, because intravaginal administration offers the benefit of delivering the drug directly and rapidly to the intended site of action, while avoiding the first-pass effect associated with, for example, oral administration.

Progesterone also can also be used to treat central nervous system injury, including traumatic central nervous system injury (such as traumatic brain injury (TBI)) and ischemic stroke. For example, recent studies have shown that treatment with progesterone can limit tissue damage and improves functional outcome after blunt TBI, stroke, spinal cord injury, diabetic neuropathies, and other types of acute neuroinjury in several species. Sayeed & Stein, in PROGRESS IN BRAIN RES. Vol. 175: 219-37 (J. Verhaagen et al., eds.) (Elsevier B. V. 2009). In clinical studies, progesterone has been administered intravenously, using formulations that are prepared shortly before use. This limits the circumstances under which progesterone can be used in emergency situations, such as when a subject has suffered TBI or ischemic stroke.

There is a need, therefore, for alternative formulations of active agents, such as progesterone, such as a dry formulation for transmucosal administration, such as nasal administration or intravaginal administration.

There also is a need for alternative formulations of other active agents, such as mometasone, including mometasone furoate, such as a dry formulation for transmucosal administration, such as nasal administration.

SUMMARY

Described herein are dry pharmaceutical compositions for transmucosal administration, comprising spray-dried particles comprising pharmaceutically active agent nanoparticles, binder, and a pharmaceutically acceptable carrier, wherein the active agent nanoparticles have an average particle size diameter prior to spray-drying of less than about 1 µm and wherein up to 10% of the spray-dried particles have a particle size of less than 10 µm, at least 50% of the spray-dried particles have a particle size of at least about 15 µm, and at least 90% of the spray-dried particles have a particle size of up to about 55 µm. In some embodiments, the active agent is progesterone, or a metabolite, derivative or prodrug thereof. In some embodiments, the active agent is mometasone, or a metabolite, derivative or prodrug thereof, such as mometasone furoate.

In some embodiments, the carrier comprises microcrystalline cellulose (MCC). In some embodiments, the binder is selected from the group consisting of hydroxypropyl methyl cellulose (HPMC) and sodium carboxymethylcelluose (NaCMC). In some embodiments, the composition further comprises a milling aid.

In some embodiments, the composition further comprises one or more pharmaceutically acceptable excipients, such as microcrystalline cellulose having an average particle size diameter from about 30 to about 150 µm, starch, or a mixture thereof and/or tribasic calcium phosphate.

In some embodiments, greater than 90% of the active agent is released from the composition within 60 minutes, when tested via dissolution testing.

In some embodiments, the compositions are formulated for intranasal administration. In some embodiments, the compositions are formulated for intravaginal administration.

Also described herein are methods for preparing a dry pharmaceutical composition for transmucosal administration as described herein, comprising spray-drying an aqueous composition comprising pharmaceutically active agent nanoparticles, binder, and a pharmaceutically acceptable carrier to obtain spray-dried particles, wherein the active agent nanoparticles have an average particle size diameter prior to spray-drying of less than about 1 µm and wherein up to 10% of the spray-dried particles have a particle size of less than 10 µm, at least 50% of the spray-dried particles have a particle size of at least about 15 µm, and at least 90% of the spray-dried particles have a particle size of up to about 55 µm. In some embodiments, the method comprises one or more of milling (optionally, with a milling aid), screening, sieving, and centrifugation.

In some embodiments, the weight ratio of active agent to carrier in the aqueous spray-dry composition is from about 1:1 to about 2:1. In some embodiments, the weight ratio of active agent to binder in the aqueous spray-dry composition is about 5:1 to 20:1. In some embodiments, the aqueous spray-dry composition comprises, on a weight basis, about 5 to 20% active agent, about 2 to 10% carrier, about 0.3 to 3.0% binder, about 0.2 to 1.0% milling aid and water.

In some embodiments, the methods further comprise combining the spray-dried particles with one or more pharmaceutically acceptable excipients. In some embodiments, the methods further comprise combining the spray-dried particles with crystalline cellulose and/or or starch and tribasic calcium phosphate to obtain a pharmaceutical composition comprising microcrystalline cellulose having an average particle size diameter from about 30 to about 150 μm, starch, or a mixture thereof, and tribasic calcium phosphate.

Also provided are dry pharmaceutical compositions for transmucosal administration, comprising spray-dried particles made by any process as described herein.

Also provided are methods of administering an active agent, comprising transmucosally administering a dry pharmaceutical composition as described herein. In some embodiments, the methods comprise intranasally administering the composition. In some embodiments, the methods comprise intravaginally administering the composition.

DETAILED DESCRIPTION

Figure 1:
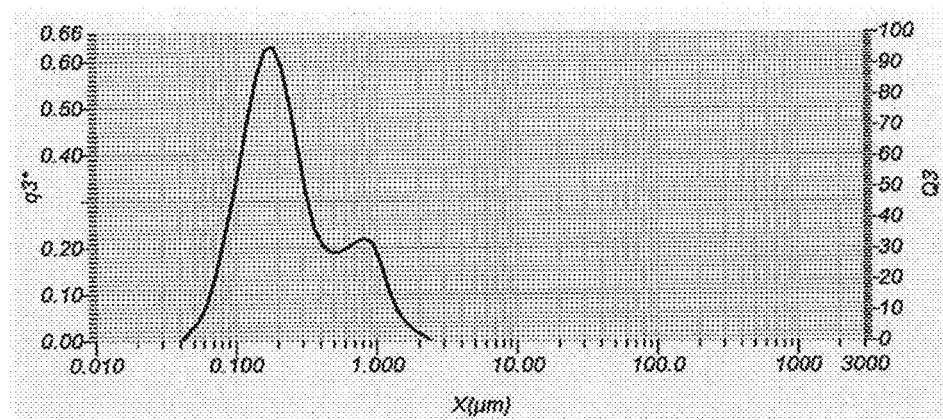
FIG. 1 depicts the particle size distribution of progesterone nanoparticles described herein. The median particle size diameter is about 0.2 μm, the D10 particle size diameter is about 0.1 μm, and the D90 particle size diameter is about 0.8 μm.

Described herein are dry pharmaceutical compositions suitable for transmucosal administration, such as intranasal administration or intravaginal administration, of an active agent. The dry compositions comprise spray-dried particles comprised of active agent nanoparticles, binder and carrier. As discussed in more detail below, the sizes of the spray-dried particles and active agent nanoparticles can be selected and controlled to promote intranasal delivery, and also are suitable for intravaginal administration.

Technical and scientific terms used herein have the meanings commonly understood by one of ordinary skill in the art to which the present invention pertains, unless otherwise defined. Reference is made herein to various methodologies known to those of ordinary skill in the art. Publications and other materials setting forth such known methodologies to which reference is made are incorporated herein by reference in their entireties as though set forth in full. Any suitable materials and/or methods known to those of ordinary skill in the art can be utilized in carrying out the present invention. However, specific materials and methods are described. Materials, reagents and the like to which reference is made in the following description and examples are obtainable from commercial sources, unless otherwise noted.

As used herein, the singular forms "a", "an" and "the" designate both the singular and the plural, unless expressly stated to designate the singular only.

The term "about" and the use of ranges in general, whether or not qualified by the term about, means that the number comprehended is not limited to the exact number set forth herein, and is intended to refer to ranges substantially within the quoted range while not departing from the scope of the invention. As used herein, "about" will be understood by persons of ordinary skill in the art and will vary to some extent on the context in which it is used. If there are uses of the term which are not clear to persons of ordinary skill in the art given the context in which it is used "about" will mean up to plus or minus 10% of the particular term.

The term "dry pharmaceutical composition" as used herein refers to a pharmaceutical composition that is substantially free of water. The phrase "substantially free" as used herein means that the described composition (e.g., pharmaceutical composition) comprises less than about 5%, less than about 3%, or less than about 1% by weight, based on the total weight of the composition at issue, of the excluded component(s) (e.g., water). In some embodiments, the dry pharmaceutical composition includes no more about 0.1% by weight water, or no more than about 0.01% by weight water.

The term "spray-dried particle" as used herein has its conventional meaning in the field of pharmaceutical formulations, and refers to a particle that includes a spray-dried aggregation of pharmaceutically active agent, binder, and carrier.

The terms "pharmaceutically active agent," "active agent," "active pharmaceutical ingredient" and "API" are used interchangeably herein.

The term "nanoparticles" as used herein refers to particles that have an average particle size diameter of about 1 μm or less. Nanoparticles can be obtained from larger particles by methods known in the art, including milling, sieving, etc.

Particle size measurements can be made using laser diffraction, as is known in the art. The laser diffraction technique relies on the phenomenon that the angle of light diffracted by a particle is inversely proportional to the size of that particle. The instrument uses a laser light source to illuminate a suspension of particles, and measures the intensity of the light that is diffracted at various angles to the incident light. Based on this distribution of intensity data, the instrument uses an algorithm, based on the Mie solution to Maxwell's equations regarding the scattering of electromagnetic radiation by a sphere, to back-calculate the intensity pattern of the scattered light into a particle-size distribution.

As used herein, the phrase "therapeutically effective amount" means that drug dosage that provides the specific pharmacological response for which the drug is administered in a subject in need of such treatment. A "therapeutically effective amount" of a drug may not always be effective in treating the conditions/diseases described herein in a given patient, even though such dosage is deemed to be a therapeutically effective amount by those of skill in the art. For convenience and illustration, exemplary dosages and therapeutically effective amounts are discussed herein with reference to adult human subjects. Those skilled in the art can adjust such amounts in accordance with standard practices as needed to treat a specific subject and/or condition/disease.

Pharmaceutical Compositions

Described herein are dry pharmaceutical compositions suitable for transmucosal administration, such as intranasal administration or intravaginal administration, of an active agent. The dry compositions comprise spray-dried particles comprised of active agent nanoparticles, binder and carrier. As discussed in more detail below, the sizes of the spray-dried particles and active agent nanoparticles can be selected and controlled to promote intranasal delivery. Thus, for example, the spray-dried particles of the compositions described herein may have a particle size distribution wherein one or more of:

up to 10% of the spray-dried particles have a particle size of less than 10 μm;
at least 50% of the spray-dried particles have a particle size of at least about 15 μm; and
at least 90% of the spray-dried particles have a particle size of up to about 55 μm.

In specific embodiments, the compositions described herein exhibit one or more beneficial characteristics such as achieving rapid delivery of the active agent, bioadherence, having improved storage stability, and being amenable to packing in a ready-to-use form.

Active Agent Nanoparticles

The pharmaceutical compositions described herein include spray-dried particles that comprise active agent nanoparticles. The active agent may be any active agent that is suitable for intranasal administration, for local or systemic effect, or any active agent for which it is desirable to prepare a dry pharmaceutical composition comprising particles comprising the active agent and a binder. In some embodiments, the active agent is suitable for intranasal administration for systemic effect. In other embodiments, the active agent is suitable for intravaginal administration for systemic effect.

In accordance with some embodiments, the active agent is progesterone or a derivative, metabolite or prodrug thereof. Representative non-limiting examples of metabolites of progesterone include allopregnanolone, pregnanediol, pregnanolone, pregnanedione, 20-α-dihydroprogesterone and 17-OH-progesterone. Representative non-limiting examples of derivatives of progesterone include 5-alpha-dihydroprogesterone, 6-dehydro-retroprogesterone (dydrogesterone), hydroxyprogesterone caproate, levonorgestrel, norethindrone, norethindrone acetate, norethynodrel, norgestrel, medroxyprogesterone, chlormadinone, and megestrol, or a pharmaceutically acceptable salt or ester thereof. Other exemplary derivatives of progesterone include progesterone derivatives with 6-α-methyl, 6-methyl, 6-ene, or 6-chloro substituents moieties introduced to the progesterone structure, and 19-norprogesterones. Representative non-limiting examples of prodrugs of progesterone include esters of progesterone including 17-alpha-OH esters of progesterone.

In accordance with other embodiments, the active agent is mometasone or a derivative, metabolite or prodrug thereof. In some embodiments, the active agent is mometasone furoate, which is a prodrug of mometasone with the chemical name (11β,16α)-9,21-dichloro-11-hydroxy-16-methyl-3,20-dioxopregna-1,4-dien-17-yl2-furoate. Mometasone furoate is a glucocorticosteroid used to reduce inflammation of the skin or in the airways.

In accordance with other embodiments, the active agent is any active agent for which it is desirable to prepare a dry pharmaceutical composition comprising particles comprising the active agent and a binder, such as an anti-inflammatory agent, an antibacterial agent, an antiviral agent, an agent useful in the treatment of cancer, an anti-emetic agent, an agent useful in the treatment of cardiovascular diseases and conditions (e.g., a cardiovascular drug), a vasoconstrictor, a vasodilator, an anti-psychotic agent, an anti-depressant agent, an anesthetic, a steroid, a stimulant, a sedative, a bronchodilator, or any other agent useful in the treatment of a disease or condition, including allergies and other conditions.

In some embodiments, the active agent nanoparticles have an average particle size diameter prior to spray-drying of less than about 1 μm. Active agent nanoparticles can be obtained from larger active agent particles by methods known in the art. For example, larger particles can be milled (by media milling or jet milling), ground, sieved and/or centrifuged to produce nanoparticles having an average particle size diameter of less than about 1 μm.

In some embodiments, the active agent nanoparticles are prepared by a process that includes milling, such as media milling, high pressure milling, or jet milling.

In the process of media milling or high pressure milling, the active agent is formulated in a suspension, which may include a milling aid (i.e., dispersant), such as a surfactant. As used herein, the terms milling aid and dispersant are used interchangeably. The suspension may be aqueous or non-aqueous, such as comprising an organic liquid (e.g. an oil or alcohol). In specific embodiments, the suspension is aqueous. The suspension is combined with milling media, typically spherical beads of a hard, inert material. Particles of active agent are broken down into a smaller size through the mechanical abrasion generated by the agitation of the media beads. Laboratory-scale milling can be performed either by low-energy means, such as rolling the slurry in a container on a roller mill, or by high-energy means, such as by mixing with a rotary agitator. Suitable milling apparatuses includes conventional wet bead mills such as those manufactured by Nylacast (available from Nylacast Components, Leicester, UK), Netzsch (available from NETZSCH GmbH & Co.

Selb, Germany), Drais (available from Draiswerke, Inc, 40 Whitney Road, Mahwah, N.J. 07430, USA) and others.

As an example, the active agent nanoparticles may be prepared by a process that includes:
(a) forming a suspension comprising active agent, a milling aid, and water;
(b) milling the suspension with a first grinding media;
(c) milling the suspension with a second grinding media, where the first grinding media have a diameter that is greater than that of the second grinding media; and
(d) collecting milled active agent nanoparticles from the suspension, where the active agent nanoparticles have an average particle size diameter of less than about 1 µm.

For example, the first grinding media may have a diameter of about 1 mm to about 2 mm, while the second grinding media may have a diameter of about 0.1 mm to about 0.5 mm.

As noted above, the milling may be effected with a milling aid, such as a surfactant. The use of one or more milling aids may prevent or reduce aggregation of active agent particles during milling, and so may promote the formation of active agent nanoparticles of a desired size. Conversely, it has been found that the use of a binder in the media milling process may increase the viscosity of the milling suspension and may promote or enhance the formation of aggregates of active agent particles, thereby hampering the ability to obtain active agent nanoparticles of a desired size. Using the guidance provided herein, those skilled in the art can select and adjust the components and conditions of the milling process to obtain active agent nanoparticles of a desired size.

In accordance with some embodiments, the milling aid is a surfactant such as a polyoxyethylene sorbitan fatty acid ester, e.g., one or more of the commercially available Tweens® such as e.g., Tween 20® and Tween 80® (ICI Specialty Chemicals). In some embodiments, the milling aid is selected from the group consisting of polysorbate 20, polysorbate 80, and benzalkonium chloride.

In general, the surfactant may be an ionic surfactant or a non-ionic surfactant. If an ionic surfactant is used, it may be an anionic surfactant or a cationic surfactant. Examples of anionic surfactants include alkyl sulfates, e.g., sodium lauryl sulfate, sodium dodecylsulfate and dioctyl sodium sulfosuccinate, and alkyl carboxylates, e.g., calcium stearate. Examples of cationic surfactants include cetyl pyridinium chloride, cetyl trimethylammonium bromide, dodecyl trimethylammonium bromide and benzalkonium chloride. In specific embodiments, the surfactant is sodium lauryl sulfate such as Duponol P® (DuPont); Tritons X-200®, which is an alkyl aryl polyether sulfonate (Rohm and Haas); Crodestas F-1100, which is a mixture of sucrose stearate and sucrose distearate (Croda Inc.). Examples of non-ionic surfactants include polyoxyethylene (POE) alkylphenols, POE straight-chain alcohols, POE polyoxypropylene glycols, POE mercaptans, long-chain carboxylic acid esters such as glyceryl and poly glyceryl esters of natural fatty acids, e.g., glycerol monostearate, propylene glycol, sorbitol and POE sorbitol esters, polyoxyethylene glycol esters, poloxamers, e.g., Pluronics F68® and F108®, which are block copolymers of ethylene oxide and propylene oxide, poloxamines, e.g., Tetronic 908®, also known as Poloxamine 908®, which is a tetrafunctional block copolymer derived from sequential addition of propylene oxide and ethylene oxide to ethylenediamine (BASF Wyandotte Corporation, Parsippany, N.J.).

Additionally or alternatively, the surfactant may be a phospholipid. Exemplary phospholipids include, but are not limited to, phosphatidyl choline, phosphatidylethanolamine, phosphatidylglycerol, phosphatidic acid, and mixtures thereof. These typically have about 4 to about 22 carbon atoms, such as from about 10 to about 18 carbon atoms, and varying degrees of saturation.

In some embodiments, the milling suspension includes from about 0.01 to 5.0% wt./wt. milling aid, such as a surfactant, including from about 0.05 to 2.0% wt./wt., from about 0.5 to 1.0% wt./wt. such as about 0.5% wt./wt., or about 1.0% wt./wt. In specific embodiments, the weight/weight ratio of active agent to milling aid in the milling suspension is from about 10:1 to about 20:1. Specific embodiments are illustrated in the examples below.

The selection of the type and amount of milling aid, such as surfactant, is made in accordance with standard practices in the manufacture of pharmaceutically active agent nanoparticles. Specific embodiments are illustrated in the examples below.

Additionally or alternatively, the milling may include jet milling. Generally, jet milling involves generating a cyclonic flow of pressurized gas (e.g., nitrogen) inside a cylindrical, steel milling chamber. The material to be milled is introduced to the chamber by a vacuum produced by a venture aperture at the inlet. The centrifugal force generated by the cyclonic gas flow forces particles against the interior walls of the chamber, causing them to impinge on each other, and break into smaller particles. When the particles are reduced to a size at which the aerodynamic forces exerted on them by the exiting gas flow exceed those produced by centrifugal force, they are exhausted from the mill and are captured in a filter. Representative jet mills include spiral jet mills, loop jet mills, and fluidized bed jet mills.

Additionally or alternatively, active agent nanoparticles can be made by processes that include, or that further include, any other methods of reducing particle size, such as high pressure homogenization, recrystallization, grinding, sieving and/or centrifuging, to produce nanoparticles having an average particle size diameter of less than about 1 µm.

In some embodiments, the active agent nanoparticles consist of the pharmaceutically active, such as when the milling process is effected without the use of a milling aid or other excipients. In some embodiments, the active agent nanoparticles consist of the pharmaceutically active agent and a milling aid, such as where the milling process includes the use of a milling aid. In specific embodiments, the weight/weight ratio of active agent to milling aid in the active agent nanoparticles is from about 10:1 to about 20:1. In specific embodiments the active agent nanoparticles do not include a carrier. In specific embodiments the active agent nanoparticles do not include a binder. Thus, the active agent nanoparticles may be prepared without any carrier or binder to obtain active agent nanoparticles having an average particle size of less than about 1 µm that do not include carrier or binder material.

In some embodiments, the active agent nanoparticles have an average particle size diameter of about 0.01 µm, 0.05 µm, 0.1 µm, 0.2 µm, 0.3 µm, 0.4 µm, 0.5 µm, 0.6 µm, 0.7 µm, 0.8 µm, 0.9 µm, less than about 1 µm, or an average particle size diameter between any two of these values. In specific embodiments, the active agent nanoparticles have an average particle size diameter of greater than about 0.1 µm and less than about 1.0 µm. In specific embodiments, the active agent nanoparticles have a median particle size diameter of about 0.2 µm. In specific embodiments, up to about 10% of the active agent nanoparticles have a particle size diameter of about 0.1 µm or less. In specific embodiments, at least about 90% of the active agent nanoparticles have a particle size diameter of up to about 0.8 µm. In specific embodiments, at least about 80% of the active agent nanoparticles have a particle size diameter of between about 0.1 µm and about 0.8 µm. In very specific embodiments, the active agent nanoparticles have a median particle size diameter of about 0.2 µm, wherein up to about 10% of the active agent nanoparticles have a particle size diameter of about 0.1 µm or less and 90% of the active agent nanoparticles have a particle size diameter of up to about 0.8 µm, or wherein at least about 80% of the active agent nanoparticles have a particle size diameter of between about 0.1 µm and about 0.8 µm.

Carrier

In accordance with any embodiments described herein, the carrier may comprise any carrier suitable for use as a carrier for a spray-dried particle for a dry powder formulation for transmucosal administration, such as nasal administration or intravaginal administration. The carrier may be selected to have a particle size distribution that is consistent with the target particle size distribution of the spray-dried particles described herein. For example, the carrier may be selected to have a particle size distribution that is less than the target particle size distribution of the spray-dried particles, as discussed in more detail below.

In some embodiments, the carrier absorbs water at about pH 7.4 and temperature of about 36° C., but is not appreciably water soluble under these conditions. In other embodiments, the carrier absorbs water and/or is appreciably water soluble under those conditions.

Exemplary carriers include, for example, water absorbing and water insoluble celluloses such as crystalline cellulose (including microcrystalline cellulose), cellulose, α-cellulose, and cross-linked sodium carboxymethyl cellulose; cross-linked vinyl polymers such as cross-linked vinyl polyvinyl pyrrolidone, cross-linked carboxyvinyl polymer or its salts, cross-linked polyvinyl alcohol and polyhydroxyethylmethacrylate. Additional examples of carriers include, for example, water-absorbing and water-insoluble starches such as hydroxypropyl starch, carboxymethyl starch, cross-linked starch, amylase, amylopectin, and pectin; water-absorbing and water-insoluble proteins such as gelatin, casein; water-absorbing and water-insoluble gums such as gum Arabic, tragacanth gum, and glucomannan.

In accordance with any embodiments described herein, the carrier may be microcrystalline cellulose (MCC). Microcrystalline cellulose is available under the trade name Ceolus®, available from Asahi Kasei Corporation, including the product sold as PH-F20JP. Additionally, MCC from the FMC Corporation, available under the trade name Avicel®, including Avicel® PH-105, is suitable for use in the compositions of the invention.

Binder

In accordance with any embodiments described herein, the binder may comprise any binder suitable for use as a binder for a spray-dried particle for a dry powder formulation for nasal administration. In some embodiments, the binder is combined with the active agent nanoparticles before the active agent nanoparticles are processed (e.g., milled, etc.) to attain an average particle size of less than about 1 µm. Thus, in such embodiments, the active agent nanoparticles are processed in the presence of the binder to attain an average particle size of less than about 1 µm.

As noted above, in some embodiments, the binder absorbs water at about pH 7.4 and temperature of about 36° C., and is generally water soluble under these conditions.

Representative binders include polyacrylates, and salts thereof (e.g., sodium, potassium, ammonium), lower alkyl ethers of cellulose such as calcium carboxymethylcellulose, hydroxypropyl cellulose (HPC, HPC-SL, and HPC-L), hydroxypropyl methylcellulose (HPMC), hypromellose 2910, sodium carboxymethylcellulose (NaCMC), methylcellulose, hydroxyethylcellulose, hydroxypropylcellulose, hydroxypropylmethylcellulose phthalate, noncrystalline cellulose, oleic acid, glycerin, petrolatum white, glycerol ester of hydrogenated rosin, propylene glycol, polyethylene glycol 400, polyethylene glycols (e.g., CarboWaxs 3350® and 1450® (The Dow Chemical co.), and Carbopol 934® (Lubrizol Corp.)), polyvinyl pyrrolidone (uncrosslinked), amylase, the magnesium aluminum silicates, alcohol (dehydrated), dichlorodifluoromethane, dichlorotetrafluoroethane, norflurane, sorbitan trioleate, trichloromonofluoromethane, benzalkonium chloride, sodium citrate, acetic acid, hydroxyanisole, chlorobutanol, citric acid, citric acid monohydrate, edetate disodium, hydrochloric acid, methylparaben, polyethylene glycol 3350, potassium phosphate monobasic, propylparaben, sodium acetate, sodium chloride, sodium hydroxide, sodium phosphate, sodium phosphate dibasic anhydrous, sodium phosphate dibasic heptahydrate, sorbitol, sucralose, anhydrous dextrose, dextrose, phenylethyl alcohol, polysorbate 80, sulfuric acid, allyl-alpha-ionone, anhydrous trisodium citrate, benzethonium chloride, benzyl alcohol, butylated hydroxyanisole, butylated hydroxytoluene, caffeine, carbon dioxide, dextrose, nitrogen, polyoxyl 400 stearate, polysorbate 20, potassium sorbate, sodium phosphate dibasic dodecahydrate, sodium phosphate dibasic heptahydrate, sodium phosphate monobasic anhydrous, sodium phosphate monobasic dehydrate, mucoadhesive polymers, such as those described in Chaturvedi et al., *J. Adv. Pharm. Technol. Res.* 2(4): 215-222 2011; F-127 gelation agents such as those described in Khairnar et al., *Int. J. Pharm. Pharm. Sci.* 3: 250 (2011); derivatized chitosans such as those described in U.S. 2010/0256091; and binders described in U.S. Pat. No. 5,958,458.

Exemplary binders include polyacrylates, and salts thereof (e.g., sodium, potassium, ammonium), lower alkyl ethers of cellulose such as calcium carboxymethylcellulose, hydroxypropyl cellulose (HPC, HPC-SL, and HPC-L), hydroxypropyl methylcellulose (HPMC), hypromellose 2910, sodium carboxymethylcellulose (NaCMC), methylcellulose, hydroxyethylcellulose, hydroxypropylcellulose, hydroxypropylmethylcellulose phthalate, noncrystalline cellulose, oleic acid, glycerin, petrolatum white, glycerol ester of hydrogenated rosin, polyethylene glycols, propylene glycol and polyethylene glycol 400.

Spray-Dried Particles

As noted above, the dry compositions described herein may comprise spray-dried particles comprised of active agent nanoparticles, binder and a pharmaceutically acceptable carrier. The spray-dried particles can be made by methods known in the art for making spray-dried particles for pharmaceutical formulations. See, e.g., Masters et al., THE SPRAY-DRYING HANDBOOK, 5th Ed., Longman Scientific & Technical (1991). In general, spray drying produces particles with a relatively uniform size distribution by aerosolizing a solution or suspension of the material into a heated chamber so that the solvent evaporates, leaving dry particles of the solute.

For example, during spray drying, the spray-drier (e.g., Buchi B290) may separate a liquid stream into a solid (solute or suspension components) and vapor (solvent components). The solid is usually collected in a drum or cyclone. The input liquid stream may be sprayed through a nozzle into a hot vapor stream (e.g., air or nitrogen) and vaporized. Solids form as moisture quickly leaves the droplets. A nozzle is usually used to make the droplets very small, maximizing heat transfer and the rate of water vaporization. For example, in a typical spray-drying process, droplet sizes can range from about 20 μm to 180 μm, about 20 μm to 100 μm, or about 20 μm to 50 μm, depending on the nozzle. In some embodiments, a high pressure single fluid nozzle (50 to 300 bars) is used. In other embodiments two-fluid nozzles are used, where one fluid nozzle is for the liquid to dry and the second fluid nozzle is for compressed gas (generally air at 1 to 7 bars).

In an exemplary method, the active agent nanoparticles, binder and pharmaceutically acceptable carrier are combined to form an aqueous composition (i.e., suspension) (i.e., feedstock) and spray dried to form the spray-dried particles. In some embodiments, the aqueous composition can optionally be further diluted with water prior to spray drying. For example, in one exemplary embodiment, as shown in Table 8 below, an aqueous composition is prepared comprising progesterone (20% wt./wt.), PS20 (1% wt./wt.), MCC (10% wt./wt.), HPMC (3% wt./wt.) and water (66% wt./wt.), and this aqueous formulation is further diluted with water (e.g., 50-75% wt./wt.) prior to spray drying.

In some embodiments, the preparation of active agent nanoparticles includes milling aid, such as may be present from the milling process, which may act as a dispersant in the spray-dry process. Optionally, a dispersant may be added to the aqueous suspension, such as those known in the art, including the surfactants discussed above, such as polysorbate 20.

As an example, the active agent nanoparticles may constitute from about 0.1 to 25.0% wt./wt. of the aqueous spray-dry composition, including about 0.5 to 5.0% wt./wt. active agent nanoparticles, including about 1.0% wt./wt. active agent nanoparticles. In specific embodiments, the aqueous spray-dry composition comprises about 5.0 to 20.0% wt./wt. active agent nanoparticles, including about 5.0, 6.0, 7.0, 8.0, 9.0, 10.0, 11.0, 12.0, 13.0, 14.0 and 15.0 wt./wt. active agent nanoparticles, such as such as 9.0, 10.0, 15.0 or 20.0% wt./wt. active agent nanoparticles. In other specific embodiments, the aqueous spray-dry composition comprises about 0.3 to 1.0% wt./wt. active agent nanoparticles, including about 0.3, 0.4, 0.5, 0.6, 0.7, 0.8, 0.9, and 1.0% wt./wt. active agent nanoparticles.

As an example, the carrier (such as MCC) may constitute from about 0.1 to 25.0% wt./wt. of the aqueous spray-dry composition. In specific embodiments the aqueous spray-dry composition comprises about 2.0 to 15.0% wt./wt. carrier, including about 2.5 to 5.0% wt./wt., about 5.0 to 7.0% wt./wt., about 7.0 to 12.0% wt./wt. carrier, including 8.0, 9.0, 10.0, and 11.0 wt./wt. carrier, such as 9.0 or 10.0% wt./wt. carrier. In other specific embodiments, the aqueous spray-dry composition comprises about 5.0, 6.0, 7.0% wt./wt. carrier.

As an example, the binder (such as HPMC or NaCMC) may constitute from about 0.01 to 5.0% wt./wt. of the aqueous spray-dry composition. In specific embodiments, the aqueous spray-dry composition comprises about 0.3 to 4.0% wt./wt. binder, including 0.375, 0.75, 1.0, 1.5, 2.0, 2.5 or 3.0% wt./wt. binding agent, such as about 1.0% wt./wt. binding agent. In other specific embodiments, the aqueous spray-dry composition comprises about 1.8 to 3.0% wt./wt. binder.

The relative amounts of active agent, binder, and carrier may vary depending on the specific active agent, binder, and carrier being used and the desired make-up of the dry particles and dry pharmaceutical composition. In exemplary embodiments, the weight/weight ratio of active agent to carrier in the aqueous spray-dry composition is from about 1:1 to about 2:1, including about 1.5:1, with more active agent than carrier. In exemplary embodiments, the weight/weight ratio of active agent to binder in the aqueous spray-dry composition is from about 5:1 to about 20:1, including from about 10:1.5 to 20:1.5, including about 10:1. In other exemplary embodiments, the weight/weight ratio of active agent to binder in the aqueous spray-dry composition is from about 1:2 to about 1:20, such as from about 1:5 to about 1:15, including about 1:10, with less active agent than carrier.

In specific embodiments the active agent, milling aid, carrier, and binder are, respectively, progesterone, polysorbate 20, MCC and HPMC.

In other specific embodiments the active agent, milling aid carrier, and binder are, respectively, mometasone furoate, benzalkonium chloride, MCC and HPMC.

In exemplary embodiments, the spray-dried particles comprise about 10.0 to 75.0% wt./wt. active agent (such as progesterone), including about 40 to 70.0% wt./wt. active agent, such as about 45.0 (including 45.5), about 50.0 (including about 52), about 55, about 60 (including about 59, 61 and 62), and about 65% wt./wt. active agent. In other embodiments, the spray-dried particles include at least about 10%, 25.0%, 40.0%, 45.0%, 50.0%, or 75.0%, or more, active agent (wt./wt.).

In other embodiments, the spray-dried particles comprise about 1.0 to 25.0% wt./wt. active agent, such as about 5% to about 10% wt./wt, including about 6.0% to about 7% wt./wt. These latter embodiments are illustrated below with mometasone furorate as the active agent.

In exemplary embodiments, the spray-dried particles comprise about 10.0 to 60.0% wt./wt. carrier (such as MCC), for example, about 25.0 to 50.0% wt./wt. carrier, or about 30.0 to 46.0% wt./wt. carrier, such as about 31%, 36%, or 45.5% wt./wt. carrier. In further exemplary embodiments, the spray-dried particles comprise about 30, 31, 34, 35 or 36% wt./wt. carrier. These embodiments are illustrated below with progesterone as the active agent.

In further exemplary embodiments, the spray-dried particles comprise about 60.0 to 80.0% wt./wt. carrier (such as MCC), for example, about 60.0 to 70.0% wt./wt. carrier. These embodiments are illustrated below with mometasone furorate as the active agent.

In exemplary embodiments, the spray-dried particles comprise from about 1.0 to 15.0% wt./wt. binder (such as HPMC or NaCMC), including about 1.0 to 8.0% wt./wt., or about 2.5 to 5.0% wt./wt., such as about 3.1% wt./wt. or about 3.7% wt./wt. binder. In further exemplary embodiments, the spray-dried particles comprise from about 4.0 to 6.0% wt./wt., such as about 4.0% wt./wt. or about 4.5% wt./wt. binder. In other exemplary embodiments, the spray-dried particles comprise about 5.5, about 9 or about 10.5% wt./wt. binder. These embodiments are illustrated below with progesterone as the active agent.

In further exemplary embodiments, the spray-dried particles comprise a greater amount of binder, such as from about 10.0 to 50.0% wt./wt. binder (such as HPMC or NaCMC), including about 20.0 or about 30.0% wt./wt binder. These embodiments are illustrated below with mometasone furorate as the active agent.

In some embodiments, the amount of binder (e.g., HPMC) is selected and controlled to select and control the particle size diameter of the spray-dried particles. For example, in Example 4 below, increasing the HPMC content from about 1.5% to about 3.0% wt./wt. resulted in spray-dried particles with a larger particle size diameter. These particles also exhibited a slower release rate of the drug.

As discussed above and illustrated in the examples below, a milling aid or surfactant may be used to prepare the active agent nanoparticles, in which case the spray-dried particles may include milling aid or surfactant (such as benzalkonium chloride, Tween 20® or Tween 80C)). In these embodiments, such components may constitute up to about 2.0% wt./wt. of the aqueous suspension and/or up to about 5.0% of the spray-dried particles. In some embodiments, such components may constitute up to about 0.1% wt./wt. of the aqueous suspension, such as about 0.05 to about 0.07% wt./wt., and/or up to about 1.0% of the spray-dried particles, such as about 0.5 to about 0.7% wt./wt. These latter embodiments are illustrated below with mometasone furorate as the active agent.

In some embodiments, the aqueous spray-dry composition includes, on a weight/weight basis, about 9% active agent, about 9% carrier, about 0.9% binder, about 0.9% milling aid, and water. In other embodiments, the aqueous spray-dry composition includes, on a weight/weight basis, about 10, 15 or 20% active agent, about 10% carrier, about 1, 1.5 or 3% binder, about 1% milling aid, and water. These embodiments are illustrated below with progesterone as the active agent.

In other embodiments, the aqueous spray-dry composition includes, on a weight/weight basis, about 0.6 or 0.7% active agent, about 6-7% carrier, about 1.8-3% binder, about 0.06-0.07% milling aid, and water. These embodiments are illustrated below with mometasone furorate as the active agent.

In accordance with any of the embodiments described herein, the active agent may constitute about 40 to about 75% wt./wt., including about 60%, about 65%, and about 70% wt./wt. of the spray-dried particles. In specific embodiments, the carrier may constitute about 25 to about 50% wt./wt. (including about 30% wt./wt.) of the spray-dried particles. In further specific embodiments, the binder may constitute about 1 to about 15% wt./wt. (including about 5% or about 10% wt./wt.) of the spray-dried particles. In specific embodiments, the milling aid may constitute about 0.1 to about 5.0% wt./wt. (including about 2% and about 4% wt./wt.) of the spray-dried particles. These embodiments are illustrated below with progesterone as the active agent.

Alternatively, in accordance with any of the embodiments described herein, the active agent may constitute about 6-7% wt./wt. of the spray-dried particles. In specific embodiments, the carrier may constitute about 60 to about 70% (including about 61 to about 70) wt./wt. of the spray-dried particles. In further specific embodiments, the binder may constitute about 20 to about 30 (including about 21 to about 31) % wt./wt. of the spray-dried particles. In other specific embodiments, the milling aid may constitute about 0.6-0.7% wt./wt. of the spray-dried particles. These embodiments are illustrated below with mometasone furoate as the active agent.

In specific embodiments, the size of the spray-dried particles is selected and controlled to achieve nasal delivery of the active agent while avoiding or minimizing pulmonary delivery. For example, particles with an average particle size diameter of about 100 μm are large enough to successfully impact the nasal mucosa, but may not be absorbed sufficiently through nasal mucosa. On the other hand, smaller particles (e.g., particles with an average particle size diameter of about 2 μm) may be too readily inhaled into the lungs (pulmonary delivery). In general, particles with an average particle size diameter of about 10 μm or greater may be absorbed intranasally, while particles with an average particle size diameter of about 5 μm or less may be absorbed into the lungs. Thus, for example, the spray-dried particles of the compositions described herein may have a particle size distribution wherein:

up to 10% of the spray-dried particles have a particle size of less than 10 μm;

at least 50% of the spray-dried particles have a particle size of at least about 15 μm; and at least 90% of the spray-dried particles have a particle size of up to about 55 μm.

In specific embodiments, the size of the spray-dried particles is selected and controlled by selecting and controlling the spray-drying parameters, as is known in the art, in accordance with the guidance provided above and as illustrated in the examples. Representative non-limiting examples of parameters that can be varied during the spray-drying process include solvents, starting material concentrations, flow-rates of the injected materials and/or air, and process temperatures. Additionally or alternatively, the size of the spray-dried particles can be selected and controlled by processes that include, or that further include, for example, sieving and/or centrifuging.

In some embodiments, the spray-dried particles exhibit good release of the active agent. For example, dissolution testing can be carried out in accordance with USP II (Apparatus 2, Paddle) at 75 RPM, 37° C., in a dissolution medium of 900 ml 1.0% Tween®80 in phosphate buffered saline (PBS) at pH 7.4. In some embodiments, the spray-dried particles exhibit greater than 90% release of the active agent within 60 minutes, within 30 minutes, within 20 minutes, within 15 minutes, or shorter, when tested by this method, as illustrated in the examples below.

Other Dry Particles

Although the discussion above focuses on spray-dried particles, the dry compositions described herein may comprise dry particles prepared by methods other than spray drying. For example, dry particles comprising active agent bound to a carrier may be prepared by any method known in the art for physically binding one particle to another, such as spray-drying, wet granulation, dry granulation, and fluid bed processing. In some embodiments, at least about 50% of the active agent nanoparticles are bound to carrier particles, including at least 75%, and at least 80%.

The identity and relative amounts of active agent, binder and carrier for dry particles prepared by methods other than spray drying can be the same as those described above for spray-dried particles. Thus, the identity and relative amounts of active agent, binder and carrier discussed above for spray-dried particles should be understood as applying to embodiments wherein the dry particles are prepared by methods other than spray drying, although such components and relative amounts can be modified in accordance with routine practices in the art.

In wet granulation, granules (i.e., particles) are formed by the addition of a granulation liquid (e.g., comprising binder and solvent) onto a powder bed which is under the influence of an impeller (such as screws in a high shear granulator or air in a fluidized bed granulator). In some embodiments, the nanoparticles are introduced with the carrier particles or are dispersed in the granulation liquid (e.g., with the binder). The wetting and agitation of wet granulation processing leads to the active agent nanoparticles being bound to particles of the carrier material (e.g., MCC). The solvent of the granulation liquid (which is typically water or a volatile solvent such as ethanol or isopropanol) is removed to obtain dry particles comprising active agent nanoparticles bound to carrier.

In dry granulation, no granulation liquid is used. Instead, granules are formed by compacting and densifying the dry components, such as by using high pressure. A Sweying granulator or high shear mixer-granulator are examples of equipment that can be used for dry granulation. The process results in dry particles comprising active agent nanoparticles bound to carrier.

In fluid bed processing, a fluidized bed of dry powder composition is placed under appropriate conditions to cause the dry powder composition to behave as a fluid. This is typically done by forcing pressurized air, gas, or other fluids through the bed of dry powder composition. This causes the dry powder composition to acquire properties and attributes similar to those of normal fluids, resulting in what is known as fluidization. Thus, fluid bed processing can be used to form dry particles comprising active agent nanoparticles bound to carrier.

Optional Additives

The compositions described herein may optionally include one or more pharmaceutically acceptable excipients. Suitable excipients are described in the Handbook of Pharmaceutical Excipients, Pharmaceutical Press, 2012, published by The American Pharmaceutical Association and The Royal Pharmaceutical Society of Great Britain.

Exemplary pharmaceutically acceptable excipients include acidifying, alkalizing, binding, chelating, complexing, and/or solubilizing agents, antiseptics, preservatives, including antimicrobials, e.g., methyl- and propylhydroxybenzoates, antioxidants, e.g., a-tocopherol or ascorbyl palmitate, stabilizing agents, viscosity modifying agents, solvents, diluents, lubricating agents such as talc, magnesium stearate and mineral oil, wetting agents, emulsifying and suspending agents, flavoring agents, therapeutic agents, polyols, buffers, and inert fillers.

In some embodiments, the spray-dried particles are formulated with excipients selected to improve the flowability of the dry composition, such as described, for example, in EP 2 116 264, the entire contents of which are incorporated herein by reference in their entirety. For example, the composition may include a microcrystalline cellulose with a smaller particle size diameter, a microcrystalline cellulose with a larger particle size diameter, and tribasic calcium phosphate. In particular, the formulation may include a first crystalline cellulose that has an untapped bulk density of 0.13 to 0.29 g/cm$^3$, a specific surface area of 1.3 m$^2$/g or more, an average particle diameter of 30 μm or less, and an angle of repose of 55° or more; a second crystalline cellulose that has an untapped bulk density of 0.26 to 0.48 g/cm$^3$, a specific surface area of 1.3 m$^2$/g or less, an angle of repose of 50° or less, and an average particle diameter of 150 μm or less, such as from about 30 to about 150 μm, such as from about 30 to about 100 μm, including from about 40 to about 75 μm, and tribasic calcium phosphate, or any one or more of such components. In particular, the microcrystalline cellulose with a larger particle size diameter is believed to improve flowability of the composition. In specific embodiments, the composition includes about 5.0 to 30.0% wt./wt. microcrystalline cellulose of the larger particle size diameter or starch (or a mixture thereof), such as about 10% wt./wt. microcrystalline cellulose of the larger particle size diameter or starch (or a mixture thereof), and about 0.1 to 10% wt./wt. tribasic calcium phosphate, including about 1% wt./wt. tribasic calcium phosphate, based on the total weight of the pharmaceutical composition. Alternatively, the spray-dried particles described herein are formulated with a flowability improving composition comprising a first microcrystalline cellulose, a second microcrystalline cellulose, and tribasic calcium phosphate, wherein the amount of tribasic calcium phosphate constitutes from about 0.1 to 10% wt./wt/ of the flowability improving composition and the second microcrystalline cellulose constitutes from about 5 to about 30% wt./wt/ of the flowability improving composition. In some embodiments, the first microcrystalline cellulose is provided as a component of the spray-dried particles, or, optionally, is not present, such that the composition comprises the spray-dried particles, microcrystalline cellulose having an average particle size diameter of from about 30 to about 150 μm, and tribasic calcium phosphate.

Thus, the spray-dried particles described herein may optionally be formulated with one or more optional pharmaceutically acceptable excipients to form a final dry pharmaceutical composition.

In specific embodiments, the compositions are sterile. In some embodiments, the compositions meets the requirements of one or more of USP Chapter <71> (sterile), USP Chapter <85> ("Bacterial endotoxin test,") and USP Chapter <151> ("pyrogen test").

The compositions of the present invention may be provided in ready-to-use form. "Ready-to-use" as used herein means that no further formulation, such as diluting or mixing together of multiple components, is required.

The compositions may be provided in sealed packaging suitable for use with dry formulations. In specific embodiments, the composition is packaged in a sealed container. The container may be overwrapped to provide protection from the physical environment.

In some embodiments, the compositions are provided in a sterile, ready-to-use form, and have a shelf life of at least one year, three years, five years or seven years at room temperature.

Intravaginal Administration

The dry pharmaceutical compositions described herein may be administered intravaginally using methods, applicators, and/or devices known in the art.

Intranasal Administration

The dry pharmaceutical compositions described herein may be administered intranasally using methods, applicators, and/or devices known in the art.

In some embodiments, the dry composition is formulated for use in a nasal spray pumps having unit dose systems for nasal powder formulations available from Aptar Inc., (Crystal Lake, Ill.); breath-powered nasal delivery technology available from OptiNose Inc., (Yardley, Pa.); TriVair™ "nasal straw" delivery technology available from Trimel Inc., (Mississauga, Ontario); MicroDose™ Dry Powder Inhaler (DPI), MicroDose™ Dry Powder Nebulizer (DPN), and "electric" atomizing nasal applicators available from MicroDoseTherapeutx Inc., (Monmouth Junction, N.J.); and monodose insufflators available from MIAT S.p.A. (Milan, Italy).

In some embodiments, the dry composition is formulated for use in a DPI device, such as the DPI noted above, or is dispersed in a propellant for use in pressurized metered dose inhalers (PMDIs). DPIs normally rely upon a burst of inspired air that is drawn through the unit to deliver a drug dosage. Such devices are described in, for example, U.S. Pat. No. 4,807,814, which is directed to a pneumatic powder ejector having a suction stage and an injection stage, and U.S. Pat. No. 5,785,049, directed to dry powder delivery devices for drugs. For use in a PDMI, the composition may be formulated as a suspension in a suitable propellant such as a halogenated hydrocarbon. PMDIs are described in, for example, Newman, S.P., Aerosols and the Lung, Clarke et al., eds., pp. 197-224 (Butterworth's, London, England, 1984). PMDIs release a metered dose upon each actuation.

In some embodiments the composition is administered by the use of an intranasal insufflator. An insufflator may include a fixed-dose dispensing mechanism to deliver a substantially fixed dose of the composition.

Other Routes Of Administration

The compositions described herein also can be administered by other routes. For example, in some embodiments, the dry pharmaceutical compositions described herein may be used for oral, buccal or ocular administration. Additionally or alternatively, the dry compositions can be prepared for administration by injection or infusion, such as intravenous, subcutaneous or intramuscular administration.

Methods of Treatment

The dry pharmaceutical compositions described herein are suitable for transmucosal administration for treating any condition treated by transmucosal administration of the active agent, such as for local, regional or systemic effect. Additionally, as noted above, the dry pharmaceutical compositions described herein are suitable for administration by other routes, for treating any condition treated by the active agent, such as for local, regional or systemic effect.

In specific embodiments where the active agent is progesterone, the dry pharmaceutical compositions are useful in any therapeutic method where progesterone is useful for local, regional or systemic effect, such as for treating low progesterone levels in subjects in need thereof, including female subjects undergoing in vitro fertilization procedures, experiencing or at-risk of pre-term labor, in need of menstrual cycle regulation, etc.

The dry pharmaceutical compositions described herein comprising progesterone also are useful for treating traumatic or ischemic central nervous system injury in a subject, including a human subject, such as traumatic brain injury or stroke, such as by intranasally delivering the composition to a subject in need thereof, such as a subject suffering from traumatic or ischemic central nervous system injury, such as traumatic brain injury or stroke.

In specific embodiments where the active agent is mometasone or mometasone furoate, the dry pharmaceutical compositions are useful in any therapeutic method where mometasone or mometasone furoate is useful for local, regional or systemic effect, such as for treating asthma or inflammatory disorders such as nasal sinus inflammation, etc.

In some embodiments, the dry pharmaceutical compositions described herein are suitable for administration to patients in a hospital setting such as in an intensive care unit. In other embodiments, the dry pharmaceutical compositions described herein are suitable for administration to patients in an emergent setting, such as at the site of injury, or in an ambulance, or in an out-patient setting, or in a setting unsupervised by a medical professional (e.g., at home). For example, the dry pharmaceutical compositions described herein can be intranasally or intravaginally administered to the patient before the patient is admitted to a hospital, after the patient leaves a hospital, or before, during or after treatment on an out-patient basis, in a physician's office, in any clinical setting, or in a setting unsupervised by a medical professional. In some embodiments, the dry pharmaceutical compositions described herein can be intranasally or intravaginally administered as a follow-up treatment for patients after they have been treated in a hospital with an intravenous, intramuscular, or other formulation of progesterone. In some embodiments, the patient is an ambulatory patient who has suffered central nervous system (CNS) injury but does not require hospital admission, or has been discharged from a hospital, or has been treated and released from an out-patient or other clinical setting.

By "treatment" is intended any improvement in the subject, including both improved morphological recovery (i.e., enhanced tissue viability) and/or behavioral recovery and/or amelioration, regression, or recovery from a disease or condition. The improvement can be characterized as an increase in either the rate and/or the extent of behavioral and/or anatomical and/or physiological recovery following the injury or event or disease or condition. Treatment may result in a "positive therapeutic response" that includes both a complete response and a partial response.

The methods may comprise administering a therapeutically effective amount of active agent, such as progesterone. By "therapeutically effective amount of progesterone" is meant an amount of progestogen that is sufficient to elicit a therapeutic effect, as discussed above, such as an amount effective to increase serum levels of progesterone and/or exhibit a neuroprotective effect. By "therapeutically effective amount of mometasone or mometasone furoate" is meant an amount of mometasone or mometasone furoate that is sufficient to elicit a therapeutic effect, as discussed above, such as an amount effective to increase serum levels of mometasone and/or exhibit an anti-inflammatory effect.

In general, up to about 20 to 50 mg of powder can be administered per nostril. Thus, for example, a dose may include about 35 mg of active agent per nostril, such as when about 50 mg of spray-dried particles comprising about 70% active agent is administered. In some embodiments, the does includes about 1 mg, about 5 mg, about 10 mg, about 15 mg, about 20 mg, about 25 mg, about 30 mg, about 35 mg, or about 40 mg active agent per nostril, or any amount within any of these values. These doses may be particularly suitable when the active agent is progesterone. When the active agent is mometasone, lower doses of active agent may be required, such as about 100 µg (0.1 mg) per nostril per day for an adult subject, and about 50 µg (0.05 mg) per nostril per day for a pediatric subject.

Having now generally described this invention, the same will be better understood by reference to certain specific examples which are included herein for purposes of illustration only, and are not intended to be limiting of the invention.

EXAMPLES

Example 1

Media Milling of Progesterone to Form Nanoparticles

Several experimental systems were developed to assess the ability to form progesterone nanoparticles (having average particle size diameters <1 µm) by media milling, as shown in Table 1 below. Particle-size measurements were characterized from laser diffraction testing (Horiba LA-950 V2).

Media milling of the progesterone was performed using yttria-stabilized zirconia (YTZ) beads. Suspensions 1-9 were milled using 0.5 mm media. Suspensions 10 and 11 were milled sequentially, first using 2 mm media followed by extraction and milling with 0.5 mm media. Such sequential milling yielded nanoparticles of progesterone, as desired.

Nanoparticles were prepared from 10% progesterone suspensions in the presence of 0.5% benzylalkonium chloride (BAC) or 1% polysorbate surfactants such as polysorbate 20 (PS20) or polysorbate 80 (PS80). Suspensions with and without binders such as hydroxypropyl methyl cellulose (HPMC) and sodium carboxymethylcelluose (NaCMC) were assessed. The presence of 1% NaCMC or HPMC yielded particle sizes larger than desired. See suspensions 1, 2, 4, 5, 7, and 8. Suspension without binders yielded nanoparticles or particles that were nearly nano-sized. See suspensions 3, 6, 9, 10, and 11.

Suspensions 10 and 11 both yielded progesterone nanoparticles having an average particle size diameter of less than about 1 μm, as desired. Nanoparticle suspension 10 was carried through to the next spray drying step.

TABLE 1

| No. | Surfactant | Binder | Media | Median PSD |
|---|---|---|---|---|
| 1 | 0.5% BAC | 1% NaCMC | 0.5 mm | 46 μm |
| 2 | 0.5% BAC | 1% HPMC | 0.5 mm | 46 μm |
| 3 | 0.5% BAC | None | 0.5 mm | 1.2 μm |
| 4 | 1% PS20 | 1% NaCMC | 0.5 mm | 52 μm |
| 5 | 1% PS20 | 1% HPMC | 0.5 mm | 31 μm |
| 6 | 1% PS20 | None | 0.5 mm | 1.8 μm |
| 7 | 1% PS80 | 1% NaCMC | 0.5 mm | 57 μm |
| 8 | 1% PS80 | 1% HPMC | 0.5 mm | 52 μm |
| 9 | 1% PS80 | None | 0.5 mm | 1.0 μm |
| 10 | 1% PS20 | None | 2 mm, 0.5 mm | 0.2 μm |
| 11 | 1% PS80 | None | 2 mm, 0.5 mm | 0.2 μm |

Example 2

Formation of Spray-Dried Particles

As noted above, nanoparticles prepared as described for suspension 10 above were used in spray drying. (The particle size distribution of these nanoparticles is depicted in FIG. 1). The nanoparticles were extracted and combined with microcrystalline cellulose (e.g., Ceolus PH-F20), HPMC, and water for spray-drying in the proportions shown below in Table 2, which shows the nominal components before and after spray drying. Two batches, A and B, of the spray-dried particles were prepared according to the conditions shown in Table 3.

TABLE 2

| Component | Before Spray Drying | After Spray Drying |
|---|---|---|
| Progesterone, nanomilled | 9.0% | 45.5% |
| Microcrystalline cellulose | 9.0% | 45.5% |
| Polysorbate 20 | 0.9% | 4.5% |
| HPMC | 0.9% | 4.5% |
| Water | 80.2% | ** |

** The final product main include some residual moisture, but it was not characterized.

Table 3 shows the spray drying process parameters used to prepare two batches, A and B, of the spray-dried particles.

TABLE 3

| Process Parameter | Batch A | Batch B |
|---|---|---|
| Inlet temperature | 110° C. | 110° C. |
| Outlet temperature | 54° C. | 54° C. |
| Aspiration | 100% | 100% |
| Pump Rate | 30% | 20% |
| Air Flow Rate | 50% | 50% |
| Nozzle Cleaner Setting | 4 | 4 |
| Nozzle Cap Size | 1.5 mm | 1.5 mm |

Shown below in Table 4 is a comparison of the particle-size distributions of the spray-dried particles from Batches A and B, and a Control Batch of microcrystalline cellulose carrier alone. Relative particle-size distributions were measured in polydimethylsiloxane to prevent dissolution of the HPMC binder. A portion of spray-dried particles from Test Batch A was subjected to stability testing. After one month storage at either −20° C., 40° C./75% Relative Humidity, or 60° C., the active agent contents of the spray-dried particles were all similar to that before storage, within the limit of the detection. As used herein, D10, D50 and D90 refer to the particle size diameter in microns at the 10th, 50th (median) and 90th percentiles, respectively.

TABLE 4

| Batch | D10 | D50 | D90 |
|---|---|---|---|
| Control | 9.4 μm | 16 μm | 35 μm |
| A | 11 μm | 21 μm | 41 μm |
| B | 11 μm | 21 μm | 52 μm |

Thus, for both batches A and B, no more than 10% of the spray-dried particles have a particle size of less than 10 μm, at least 10% of the spray-dried particles have a particle size of at least 10 μm, at least 50% have a particle size of at least about 15 μm, and at least 90% have a particle size of up to about 55 μm.

Example 3

Jet Milling of Progesterone

Jet milling was also investigated as a method for grinding progesterone.

The progesterone Batch Material C was processed at relatively high pressures (100 psi/95 psi). The particle-size results from the initial jet milling are summarized in Table 5. A subsequent batch (Batch Material D) was milled at the lowest pressure levels achievable by the jet mill, and its size distribution is shown in Table 5, as are particle-size data after each subsequent processing step (e.g., sieving, screening and centrifugation) of that Batch Material D. Two additional batches (E and F) were prepared by low-pressure jet milling of progesterone followed by passing the jet milled particles through a 45-micron sieve, and the particle-size distributions for Batches E and F also are shown in Table 5. Under these conditions, jet milling was not as effective as media milling to yield progesterone nanoparticles.

TABLE 5

| Batch Material # | Batch Material After Jet Milling | D10 | D50 | D90 |
|---|---|---|---|---|
| C | 100 psi/95 psi | 0.8 μm | 5.1 μm | 15 μm |
| D | 5 psi/5 psi | 2.7 μm | 15 μm | 43 μm |
| | Process Steps | | | |
| | After 45 μm sieve | 2.7 μm | 14 μm | 28 μm |
| | After 5 μm screen | 2.6 μm | 13 μm | 30 μm |
| | After centrifugation | 3.9 μm | 21 μm | 43 μm |
| E | 5 psi/5 psi & 45 μm sieve | 3.1 μm | 17 μm | 33 μm |
| F | 5 psi/5 psi & 45 μm sieve | 6.6 μm | 21 μm | 38 μm |

Example 4

Dissolution/Release of Progesterone

An in-vitro dissolution assay (USP II, Apparatus 2 (Paddle)) was used to determine the rate at which progesterone dissolves/is released from test compositions under simulated physiological conditions. The dissolution assay parameters are listed in Table 6.

TABLE 6

| Parameter | Setting |
| --- | --- |
| Apparatus Setup | Apparatus 2 (Paddles) |
| Paddle Speed (RPM) | 75 RPM |
| Temperature | 37° C. |
| Media | PBS pH 7.4 with 1.0% PS80 |
| Media Volume | 900 mL |
| Sample Size | 50 milligrams (~50% Drug Load) |
| Sample Time Points (min) | 5, 10, 15, 20, 30, 45, 60 min, infinity time point of 120 min (at 150 RPM) |
| Sampling Filters | 10 μm in-line followed by 1 μm PTFE |

The release assay was effected by HPLC at a detection wavelength of 243 nm, which corresponds to an ultraviolet peak characteristic of progesterone. Samples and standards were diluted with 50/50 (v/v) water/acetonitrile to a working injection concentration of approximately 50 μg/mL. Progesterone elutes at about 4.4 min. A wash-off step using all organic content was used to avoid build-up of surfactant and column fouling was used. The assay parameters are listed in Table 7.

TABLE 7

| Method Parameter | Specified Method Setting |
| --- | --- |
| Analytical Column | Waters XBridge C18, 4.6 × 150 mm, 5 micron, PN 186003116 |
| Mobile Phase | 25/75 (v/v) Water/Acetonitrile for 5 min 100% Acetonitrile wash-out (5 to 7 min), followed by reequilibration to 25/75 |
| Flow Rate | 1.0 mL/min |
| Detection Wavelength | 243 nm |
| Injection volume | 25 μL |
| Column Temperature | 30° C. |
| Run Time | 10 minutes |

Release of progesterone from spray-dried particles (average particle diameter >1 μm) as described herein comprising progesterone nanoparticles (average particle diameter <1 μm) and MCC (Sample FID-3207 below) was compared to release from a composition comprising a dry blend of micronized progesterone (average particle diameter >1 μm) and MCC PH-F20 in a 1:1 weight ratio (FID-3237 below). The media for dissolution testing was phosphate buffered saline at pH 7.4 with 1.0% PS80. The results are shown in FIG. 2.

Figure 2:
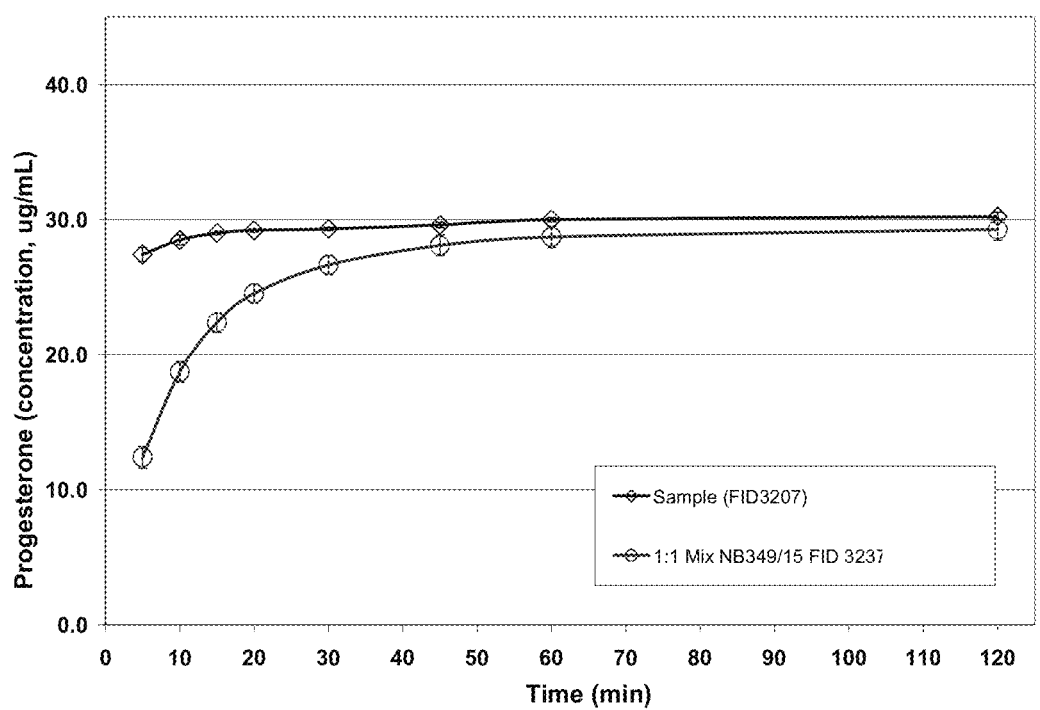
FIG. 2 depicts the release profiles of progesterone from spray-dried particles as described herein ("sample") as compared to release from a dry blend of micronized progesterone (average particle diameter >1 μm) and microcrystalline cellulose (MCC) in a 1:1 weight ratio. The spray-dried particles show complete release of progesterone in about 15 to 20 minutes, whereas the 1:1 mixture did not show complete release until about 60 minutes.

As shown in FIG. 2, the spray-dried particles (FID-3207) show complete release of progesterone in about 15 to 20 minutes, whereas the 1:1 mixture (FID-3237) did not show complete release until about 60 minutes.

Additional spray-dried particle compositions were prepared as set forth in Table 8, which shows the formulations of the aqueous compositions prior to spray drying, particle size diameters after spray drying, and theoretical and actual compositions after spray drying.

TABLE 8

| | | Sample | | | |
| --- | --- | --- | --- | --- | --- |
| Ingredient | | 5 | 6 | 7 | 8 |
| Composition Prior to Spray Drying (wt %) | Progesterone | 20 | 20 | 20 | 20 |
| | PS20 | 1 | 1 | 1 | 1 |
| | MCC (PH-F20) | 10 | 10 | 10 | 10 |
| | HPMC | 1.5 | 1.5 | 3 | 3 |
| Further dilution with H₂O (wt %) * | | 50 | 75 | 50 | 75 |
| Particle Size Diameter Of Spray Dried Powder (μm) | | 17.15 | 17.38 | 18.20 | 20.55 |
| Theoretical Composition after Spray Drying (wt %) | Progesterone | 61.54 | 61.54 | 58.82 | 58.82 |
| | PS20 | 3.08 | 3.08 | 2.94 | 2.94 |
| | MCC | 30.78 | 30.78 | 29.42 | 29.42 |
| | HPMC | 4.61 | 4.61 | 8.82 | 8.82 |
| Actual Composition After Spray Drying (wt %) | Progesterone | 67.6 | 68.1 | 64.5 | 62.5 |

* Those formulations with a 50% H₂O parameter were spray-dried at 50% of the stated solids concentrations. Those at 75%, where spray-dried at 25% of the stated solids concentrations.

Figure 3:
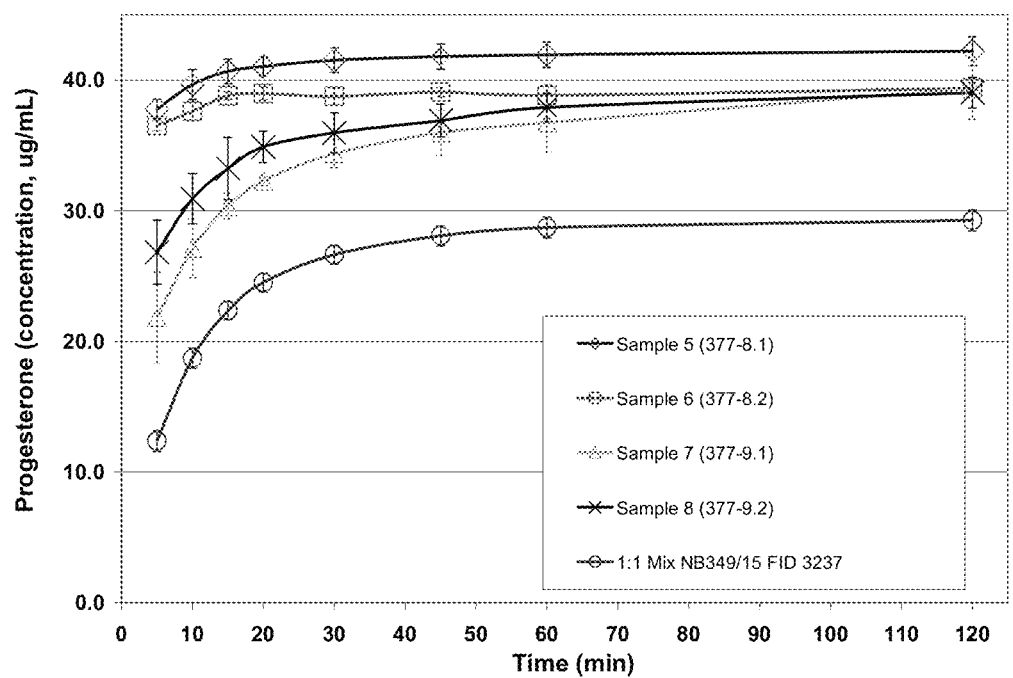
FIG. 3 depicts the release profiles of progesterone from four samples (5, 6, 7 and 8) of spray-dried particles as described herein as compared to release from a dry blend of micronized progesterone (average particle diameter >1 μm) and MCC in a 1:1 weight ratio. Samples 5 and 6 exhibit faster release of progesterone and achieved higher concentrations of progesterone in the receptor fluid (e.g., achieved greater drug release), whereas samples 7 and 8 exhibited slower release and lower concentrations of progesterone in the receptor fluid, but still faster and higher than the 1:1 mixture.
Figure 4:
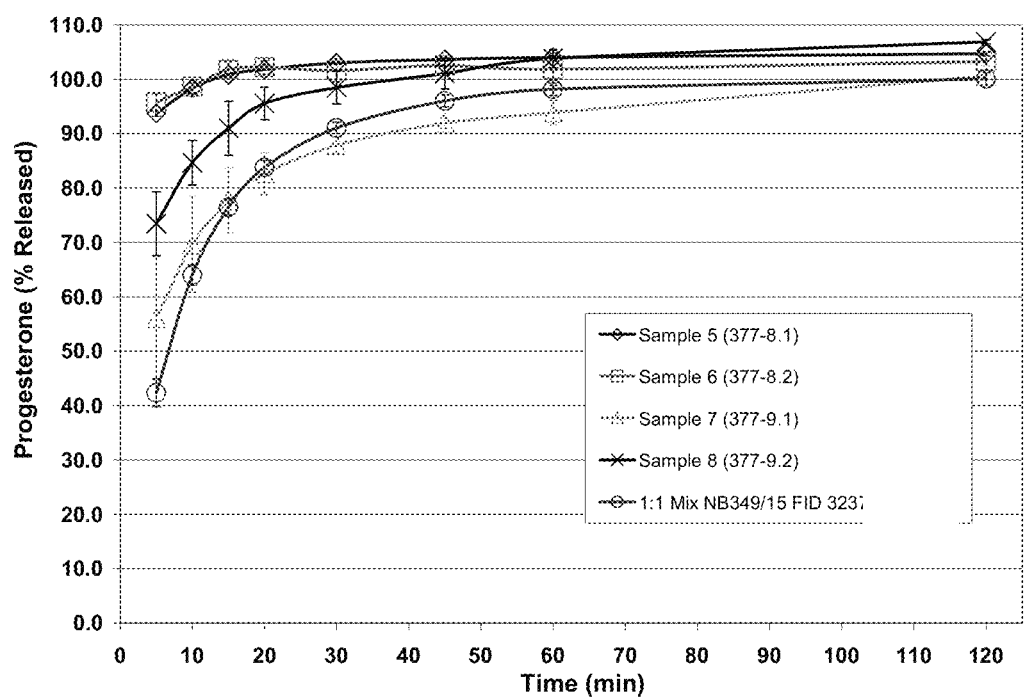
FIG. 4 depicts the release profile data of FIG. 3 as the percentage of progesterone released, and shows that Samples 5, 6 and 8 released a greater percentage of progesterone (about 100%) sooner as compared to the 1:1 mixture.

Release of progesterone from Samples 5, 6, 7 and 8 was compared to release from a composition comprising a dry blend of micronized progesterone (average particle diameter >1 μm) and MCC PH-F20 in a 1:1 weight ratio (FID-3237). The results are shown in FIG. 3. As shown in the figure, Samples 5 and 6 exhibit faster release of progesterone and achieved higher concentrations of progesterone in the receptor fluid (e.g., greater drug release), whereas samples 7 and 8 exhibited slower release and lower concentrations of progesterone in the receptor fluid, but still faster and higher than the 1:1 mixture. FIG. 4 depicts the release profile data of FIG. 3 as the percentage of progesterone released, and shows that Samples 5, 6 and 8 released of a greater percentage of progesterone (about 100%) sooner as compared to the 1:1 mixture.

Comparing Samples 5/6 and 7/8, indicates that the weight ratio of binder can be used to adjust the release rate of progesterone from the spray-dried particles described herein. Further, each of Samples 5, 6, 7 and 8 achieved higher concentrations of progesterone (e.g., released greater amounts of progesterone) than did the 1:1 mixture.

Example 5

In Vivo Comparison of Intranasal vs. Intravenous Progesterone

An in vivo study in Cynomolgus monkeys was conducted to assess and compare progesterone plasma concentration following intravenous vs. intranasal administration of progesterone, using a spray-dried composition as described herein and a 1:1 mixture as described above.

The intravenous formulation administration had a progesterone concentration of 0.25 mg/mL in an Intralipid formulation. The formulation was prepared up to 24 hours prior to dosing and was stored at room temperature and protected from light following formulation. The intravenous formulation was administered at a dose of 1 mg/kg over 2 hours at a dose volume of 4 mL/kg by infusion at a rate of 2 mL/kg/hour, corresponding to a dose of 0.5 mg/kg/hour.

The dry powder formulations for intranasal administration were administered at 25 mg/nostril using a unit dose inhaler.

Animals were administered the intravenous formulation on Study Day 1, the 1:1 mixture on Study Day 8, and the spray-dried formulation on Study Day 15.

Blood samples were collected periodically and analyzed for progesterone concentration.

Figure 5:
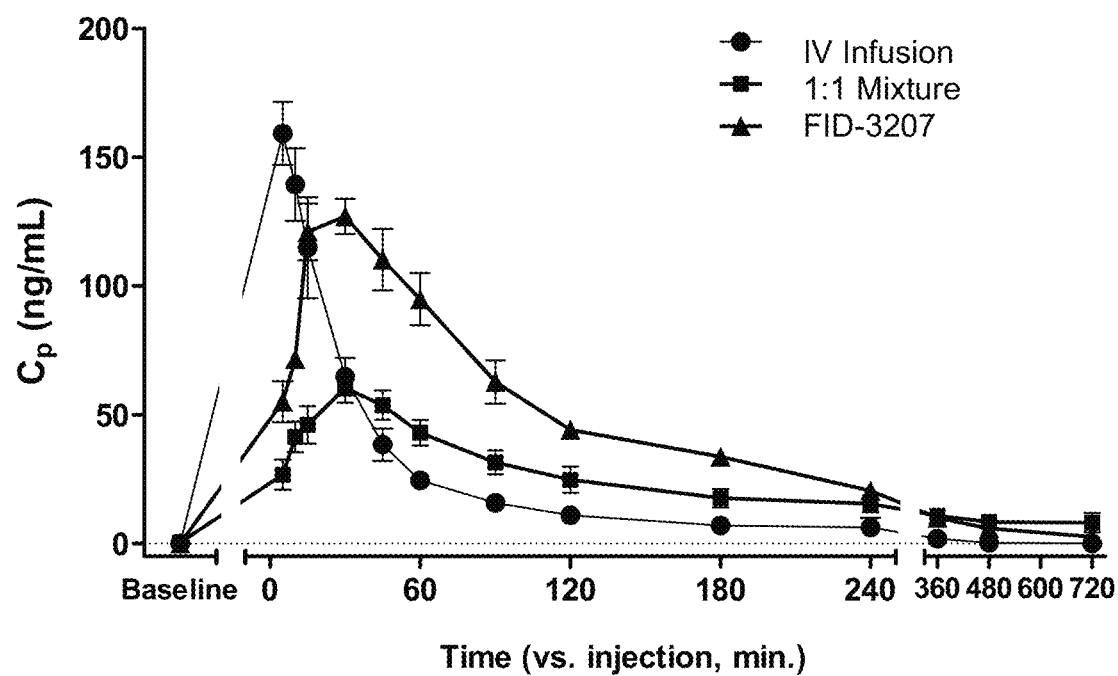
FIG. 5 depicts progesterone serum levels in monkeys after intravenous administration (i.v.) or intranasal administration of a composition comprising spray-dried particles as described herein (FID-3207) or a composition comprising micronized progesterone (average particle diameter >1 μm) and microcrystalline cellulose (MCC) in a 1:1 weight ratio (1:1 Mixture). The data show rapid absorption and elimination following nasal administration, with greater drug delivery from the spray-dried particle composition as described herein.

FIG. 5 depicts progesterone serum levels in monkeys after intravenous administration (i.v.) or intranasal administration of a composition comprising spray-dried particles as described herein (FID-3207) or a composition comprising micronized progesterone (average particle diameter >1 µm) and microcrystalline cellulose (MCC PH-F20) in a 1:1 weight ratio (1:1 Mixture). The data show rapid absorption and elimination following nasal administration, with greater drug delivery from the spray-dried particle composition as described herein.

Figure 6:
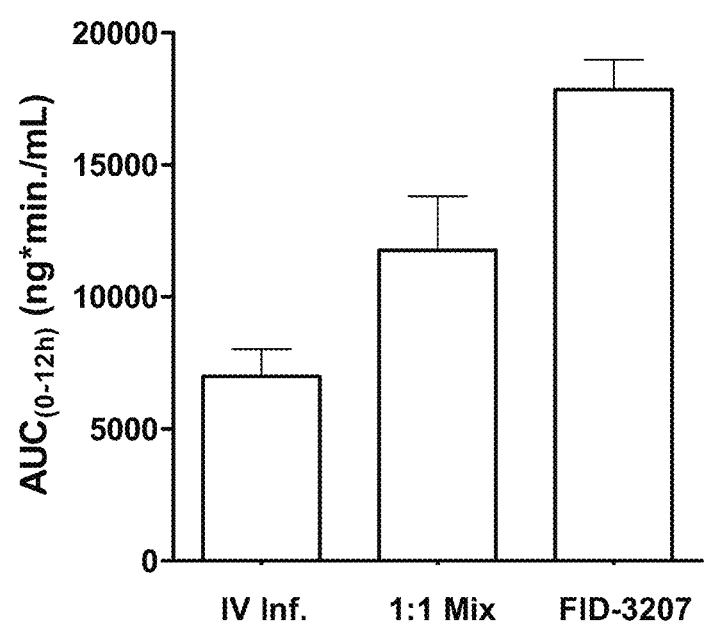
FIG. 6 depicts the area under the curve (AUC) values from the monkey study of FIG. 5. The data show greater progesterone exposure from the spray-dried particle composition as described herein than from the 1:1 mixture. (Intravenous values are not directly comparable because the dose was different, as discussed in Example 5 below).

FIG. 6 depicts the area under the curve (AUC) values from the monkey study of FIG. 5. The data show greater progesterone exposure from the spray-dried particle composition as described herein than from the 1:1 mixture. (Intravenous values are not directly comparable because the dose was different, as discussed in Example 5 below).

Figure 7:
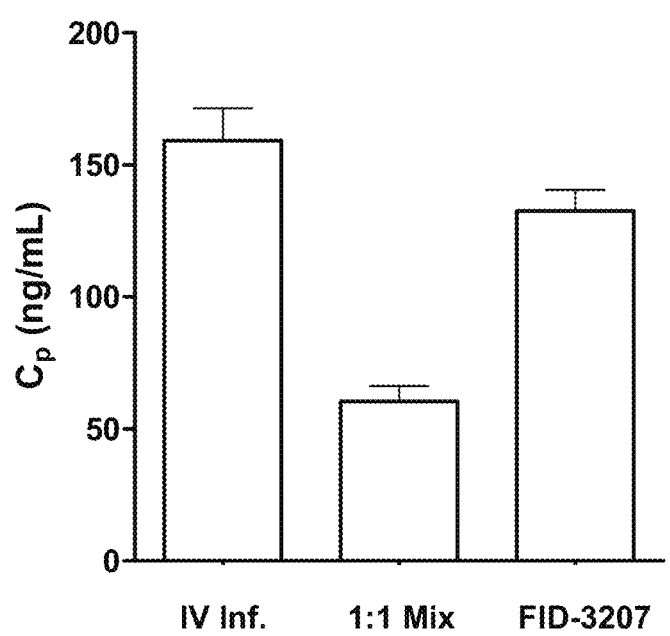
FIG. 7 depicts maximum concentration ($C_{max}$) values from the monkey study of FIG. 5. The observed maximum plasma concentration differed between groups ($F(2, 8)=22.86$, $p<0.01$). Intranasal treatment with the dry 1:1 mixture resulted in much lower maximum concentrations than either the spray-dried particle composition as described herein (FID-3207) ($p<0.01$) or i.v. treatment ($p<0.01$), while the spray-dried particle composition did not differ significantly from IV treatment ($p>0.05$).

FIG. 7 depicts maximum concentration ($C_{max}$) values from the monkey study of FIG. 5. The observed maximum plasma concentration differed between groups ($F_{(2,8)}$=22.86, $p<0.01$). Intranasal treatment with the dry 1:1 mixture resulted in much lower maximum concentrations than either the spray-dried particle composition as described herein (FID-3207) ($p<0.01$) or i.v. treatment ($p<0.01$), while the spray-dried particle composition did not differ significantly from IV treatment ($p>0.05$).

Figure 8:
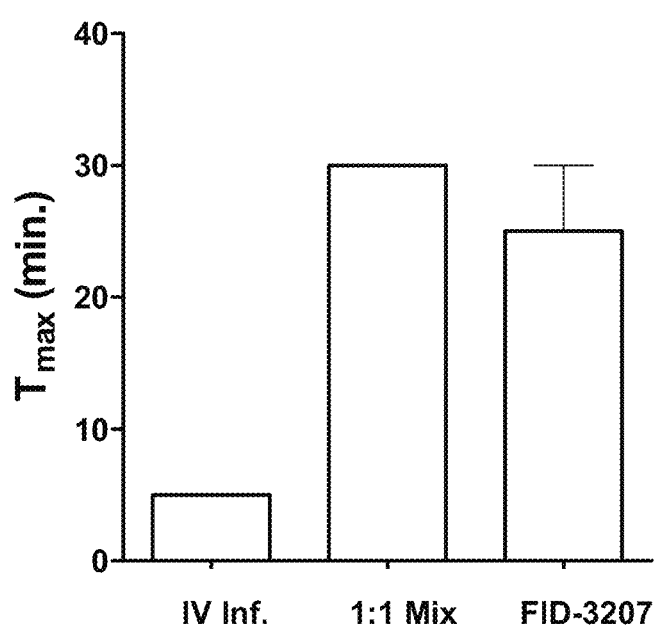
FIG. 8 depicts time to maximum concentration values ($T_{max}$) from the monkey study of FIG. 5. Statistical analysis was not conducted; however, a trend toward a short $T_{max}$ for i.v. treatment and longer $T_{max}$ for both intranasal treatments is apparent from this data.

FIG. 8 depicts time to maximum concentration values ($T_{max}$) from the monkey study of FIG. 5. Statistical analysis was not conducted; however, a trend toward a short $T_{max}$ for i.v. treatment and longer $T_{max}$ for both intranasal treatments is apparent from this data.

Example 6

In Vivo Assessment of Progesterone Concentration in the Plasma of Cynomolgus Monkeys Following a Single Nasal Administration of Several Formulations A similar in vivo study in Cynomolgus monkeys was undertaken to compare progesterone plasma concentration following intranasal administrations of progesterone, using spray-dried formulations of Samples 5 and 7 of Table 8. Results permitted an assessment of bioavailability.

The spray-dried formulations of Samples 5 and 7 of Table 8 were administered using a unit dose inhaler to the right and left nostrils of five monkeys at a dose of 0.25 mg/nostril. In particular, animals were administered the intranasal spray-dried formulation of Sample 5 on Study Day 8 and the spray-dried formulation of Sample 7 on Study Day 15. Blood was collected from each monkey via the femoral vein at 5, 10, 15, 30 and 45 minutes, and 1, 1.5, 2, 3, 4, 6, 8 and 12 hours after dosing and analyzed for progesterone concentration. Analyses of the blood samples are summarized in Table 9 below.

TABLE 9

| Group | Animal No. | $T_{max}$ (min) | $C_{max}$ (ng/mL) | $AUC_{0-t}$ (ng · min/ mL) | $AUC_{0-inf}$ (ng · min/ mL) | $T_{1/2}$ (min) |
|---|---|---|---|---|---|---|
| Sample 5 | 1 | 15.0 | 154.4 | 27910 | 29020 | 386 |
| (33.8 mg | 2 | 5.00 | 154.5 | 28880 | 30910 | 264 |
| progesterone/ | 3 | 20.0 | 164.2 | 36440 | 37950 | 375 |
| animal) | 4 | 15.0 | 112.9 | 32330 | 33210 | 283 |
|  | 5 | 15.0 | 177.1 | 37230 | 38050 | 288 |
|  | Mean | 14.0 | 152.6 | 32560 | 33830 | 319 |
|  | SD | 5.5 | 24.1 | 4250 | 4090 | 57 |
| Sample 7 | 1 | 15.0 | 196.2 | 27870 | 28160 | 110 |
| (33.2 mg | 2 | 15.0 | 185.0 | 31910 | 32390 | 268 |
| progesterone/ | 3 | 45.0 | 145.7 | 33930 | 34520 | 275 |
| animal) | 4 | 45.0 | 107.1 | 34350 | 34780 | 240 |
|  | 5 | 60.0 | 128.7 | 43260 | 44740 | 303 |
|  | Mean | 36.0 | 152.5 | 34260 | 34920 | 239 |
|  | SD | 20.1 | 37.5 | 5650 | 6100 | 76 |

Example 7

Dry Particles Of Mometasone Furoate

Dry particles comprising mometasone furoate bound to carrier are produced by spray-drying nanomilled mometasone furoate onto microcrystalline cellulose (MCC) using HPMC as a binder. The make-up of the aqueous compositions for spray-drying (e.g., the spray-dry feedstock) and spray-dry conditions are varied to evaluate the efficiency of nanoparticle attachment to the MCC carrier. The compositions of the nanomilled suspensions and the spray-drying feedstocks are described in the tables below.

Spray Drying Conditions:
Inlet temperature=110° C.; Outlet temperature=54° C.; Aspirator=100%; Pump rate=20%; Q flow=50%; Nozzle cap=1.5 mm.

Roller Milling Conditions:
Mometasone Furoate—initial median size—19.7 µm. Samples are milled in 250 mL jars for 3 hours with 0.5 mm YTZ media. Particle size diameter (PSD), after 3 hours milling, is measured in water. After milling, the suspension is extracted (needle 22G) from jars and mixed according the table and procedure shown.

Procedure for Preparation of the Spray Drying Suspensions:
The amounts of HPMC, MCC and $H_2O$ used is based on the extracted quantity of the suspension (Table II). HPMC is added as a solution prepared in $H_2O$. HPMC solution is added to the extracted suspension and mixed for 15 minutes. MCC (Grade PH-F20JP, 20 µm) is added and mixed for 15 minutes. Particle size diameter (PSD) is measured after spray drying by dispersing the spray-dried powder in a liquid such as isopropyl palmitate or silicone oil, which are non-solvents for the components and will not alter particle size or cause disintegration of the composite particle.

Materials:
Mometasone Furoate (Hovione, East Windsor, N.J.); Citric acid, anhydrous (Fisher, Hampton, N.H.); Benzalkonium chloride (Fluka, St. Louis, Mo.); Microcrystalline cellulose (AsahKasei, Glenview, Ill.); Hydroxypropylmethyl cellulose (Colorcon, Harleysville, Pa.).

Equipment:
Roller mill (US Stoneware, East Palestine, Ohio); Balance (Sartorius, Bohemia, N.Y.); Laser PSD analyzer (Horiba, Kyoto, Japan); Buchi B-290 Spray dryer (Buchi, Flawil, Switzerland).

Optical photomicrographs of the dry powder preparations (after spray-drying) reveal that mometasone furoate is associated with MCC particles. Some coalesced particles of mometasone furoate, not associated with MCC particles, also are observed. The relative proportion of mometasone furoate associated with MCC particles may be impacted by the spray-drying conditions.

TABLE 10

Roller Milling Information - 1% Mometasone Furoate

| Sample [#] | Mometasone Furoate [g] | Citric acid [g] | Benzalkonium Chloride [g] | H₂O [g] | Media [mm] | Media [g] | PSD after RM [μm] |
|---|---|---|---|---|---|---|---|
| 1 | 0.50 | 0.10 | 0.05 | 49.35 | 0.5 | 430 | 0.099 |
| 2 | 0.50 | 0.10 | 0.05 | 49.35 | 0.5 | 430 | 0.122 |
| 3 | 0.50 | 0.10 | 0.05 | 49.35 | 0.5 | 430 | 0.106 |
| 4 | 0.50 | 0.10 | 0.05 | 49.35 | 0.5 | 430 | 0.121 |

TABLE 11

Preparation of a Spray Dried Suspension

| Sample [#] | 1% Mometasone F Nanosuspension [parts] | MCC [parts] | HPMC [parts] | H₂O [parts] | PSD, Spray Dried [μm] | Spray Drying Conditions |
|---|---|---|---|---|---|---|
| 1 | 100 | 10 | 3 | 50 | 15.46 | See spray drying conditions above |
| 2 | 100 | 10 | 3 | 50 | 18.00 | Gas flow decreased from 50 to 40%. Pump from 20% to 25% |
| 3 | 100 | 10 | 3 | 30 | 17.53 | See spray drying conditions above |
| 4 | 100 | 10 | 5 | 50 | 15.96 | See spray drying conditions above |

TABLE 12

Feedstock Compositions for Spray Drying

|  | 1 |  | 2 |  | 3 |  |
|---|---|---|---|---|---|---|
| Mometasone nanosuspension | 50 | 61.35% | 50 | 69.93% | 50 | 60.61% |
| MCC | 5 | 6.13% | 5 | 6.99% | 5 | 6.06% |
| HPMC | 1.5 | 1.84% | 1.5 | 2.10% | 2.5 | 3.03% |
| H2O | 25 | 30.67% | 15 | 20.98% | 25 | 30.30% |
|  | 81.5 | 100.00% | 71.5 | 100.00% | 82.5 | 100.00% |

TABLE 13

Feedstock Compositions for Spray Drying
(Components of Mometasone Suspension Shown)

|  | 1 |  | 2 |  | 3 |  |
|---|---|---|---|---|---|---|
| Mometasone | 0.5 | 0.61% | 0.5 | 0.70% | 0.5 | 0.61% |
| Citric Acid | 0.1 | 0.12% | 0.1 | 0.14% | 0.1 | 0.12% |
| BAC | 0.05 | 0.06% | 0.05 | 0.07% | 0.05 | 0.06% |
| Water | 49.35 | 60.55% | 49.35 | 69.02% | 49.35 | 59.82% |
| MCC | 5 | 6.13% | 5 | 6.99% | 5 | 6.06% |
| HPMC | 1.5 | 1.84% | 1.5 | 2.10% | 2.5 | 3.03% |
| H2O | 25 | 30.67% | 15 | 20.98% | 25 | 30.30% |
|  | 81.5 | 100.00% | 71.5 | 100.00% | 82.5 | 100.00% |

TABLE 14

Spray-Dried Compositions

|  | 1 |  | 2 |  | 3 |  |
|---|---|---|---|---|---|---|
| Mometasone | 0.5 | 6.99% | 0.5 | 6.99% | 0.5 | 6.13% |
| citric acid | 0.1 | 1.40% | 0.1 | 1.40% | 0.1 | 1.23% |
| BAC | 0.05 | 0.70% | 0.05 | 0.70% | 0.05 | 0.61% |
| MCC | 5 | 69.93% | 5 | 69.93% | 5 | 61.35% |
| HPMC | 1.5 | 20.98% | 1.5 | 20.98% | 2.5 | 30.67% |
|  | 7.15 | 100.00% | 7.15 | 100.00% | 8.15 | 100.00% |

What is claimed:

1. A dry powder pharmaceutical composition for transmucosal administration, comprising spray-dried particles consisting of (i) pharmaceutically active agent nanoparticles consisting of pharmaceutically active agent and, optionally, a milling aid, (ii) binder, (iii) a water-insoluble pharmaceutically acceptable carrier selected from water insoluble celluloses and water-insoluble starches, and, optionally, (iv) a milling aid, wherein:
   the active agent is progesterone, or a metabolite, derivative or prodrug thereof,
   the pharmaceutically active agent nanoparticles are spray-dried onto the carrier from an aqueous suspension comprising the pharmaceutically active agent nanoparticles,
   the active agent nanoparticles have an average particle size diameter of less than about 1 μm, and
   up to 10% of the spray-dried particles have a particle size of less than 10 μm, at least 50% of the spray-dried particles have a particle size of at least about 15 μm, and at least 90% of the spray-dried particles have a particle size of up to about 55 μm.

2. The pharmaceutical composition of claim 1, wherein the water-insoluble pharmaceutically acceptable carrier is microcrystalline cellulose (MCC).

3. The pharmaceutical composition of claim 1, wherein the binder is selected from the group consisting of hydroxypropyl methyl cellulose (HPMC) and sodium carboxymethylcellulose (NaCMC).

4. The pharmaceutical composition of claim 1, wherein the milling aid is present.

5. The pharmaceutical composition of claim 4, wherein the milling aid is selected from the group consisting of polysorbate 20, polysorbate 80, and benzalkonium chloride.

6. The pharmaceutical composition o claim 1, wherein the active agent constitutes about 40 to about 75 wt% of the spray-dried particles.

7. The pharmaceutical composition of claim 1, wherein the carrier constitutes about 25 to about 50 wt% of the spray-dried particles.

8. The pharmaceutical composition of claim 1, wherein the binder constitutes about 1 to about 15 wt% of the spray-dried particles.

9. The pharmaceutical composition of claim 4, wherein the milling aid constitutes compnsos about 0.1 to about 5 wt.% of the spray-dried particles.

10. The pharmaceutical composition of claim 1, wherein the spray-dried particles consist of:
    about 40 to about 75 wt.% active agent;
    about 25 to about 50 wt.% carrier;
    about 1 to about 15 wt.% binder; and
    about 0.1 to about 5.0 wt.% milling aid.

11. The pharmaceutical composition of claim 1, wherein the spray-dried particles consist of:
    about 40 to about 75 wt.% progesterone;
    about 25 to about 50 wt.% MCC;
    about 1 to about 15 wt.% HPMC; and
    about 0.1 to about 5.0 wt.% polysorbate 20.

12. The pharmaceutical composition of claim 1, further comprising one or more pharmaceutically acceptable excipients.

13. The pharmaceutical composition of claim 1, further comprising about 5.0 to 30.0% wt./wt. of microcrystalline cellulose having an average particle size diameter from about 30 to about 150 μm, starch, or a mixture thereof and about 0.1 to 10% wt./wt. tribasic calcium phosphate.

14. The pharmaceutical composition of claim 1, wherein greater than 90% of the active agent is released from the composition within 60 minutes, when tested via dissolution testing in accordance with USP Dissolution Apparatus 2-Paddle at 75 RPM, 37° C., in a dissolution medium of 900 ml 1.0% Tween®80 in phosphate buffered saline at pH 7.4.

15. A method for preparing a dry powder pharmaceutical composition for transmucosal administration according to claim 1, comprising spray-drying an aqueous composition comprising (i) pharmaceutically active agent nanoparticles consisting of pharmaceutically active agent and, optionally, a milling aid, (ii) a binder, (iii) a water-insoluble pharmaceutically acceptable carrier selected from water insoluble celluloses and water-insoluble starches, and, optionally, a (iv) milling aid, to obtain spray-dried particles consisting of said pharmaceutically active agent nanoparticles, binder, water-insoluble pharmaceutically acceptable carrier, and, optionally, milling aid, wherein:
    the active agent is progesterone, or a metabolite, derivative or pro-drug thereof,
    the pharmaceutically active agent nanoparticles are spray-dried onto the carrier from an aqueous suspension comprising the pharmaceutically active agent nanoparticles, the active agent nanoparticies have an average particle size diameter of less than about 1 μm, and up to 10% of the spray-dried particles have a particle size of less than 10 μm, at least 50% of the spray-dried particles have a particle size of at least about 15 μm, and at least 90% of the spray-dried particles have a particle size of up to about 55 μm.

16. The method of claim 15, wherein the water-insoluble carrier is microcrystalline cellulose (MCC), and the binder is selected from the group consisting of hydroxypropyl methyl cellulose (HPMC) and sodium carboxymethylcellulose (NaCMC).

17. A dry pharmaceutical composition for transmucosal administration, comprising spray-dried particles made by a process according to claim 15.

18. A method of administering an active selected from progesterone, or a metabolite, derivative or pro-drug thereof agent, comprising transmucosally administering the dry pharmaceutical composition according to claim 1.

19. The pharmaceutical composition of claim 1, wherein the composition comprises spray-dried particles having a particle size of less than 10 μm.

20. The pharmaceutical composition of claim 1, wherein the water-insoluble carrier is selected from crystalline cellulose, microcrystalline cellulose, cellulose, α-cellulose, and cross-linked sodium carboxymethyl cellulose.

21. The pharmaceutical composition of claim 1, wherein the water-insoluble carrier is selected from hydroxypropyl starch, carboxymethyl starch, and cross-linked starch.

* * * * *

UNITED STATES PATENT AND TRADEMARK OFFICE
CERTIFICATE OF CORRECTION

| | | |
|---|---|---|
| PATENT NO. | : 10,695,295 B2 | Page 1 of 1 |
| APPLICATION NO. | : 14/195023 | |
| DATED | : June 30, 2020 | |
| INVENTOR(S) | : Lichty et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 37 days.

Signed and Sealed this
Twenty-seventh Day of December, 2022

Katherine Kelly Vidal
*Director of the United States Patent and Trademark Office*